United States Patent
Woolsey et al.

(10) Patent No.: US 12,340,880 B2
(45) Date of Patent: Jun. 24, 2025

(54) SYSTEMS AND METHODS FOR ESTIMATING A NET HEALTH CARE DEMAND OF POTENTIAL PATIENTS IN ONE OR MORE GEOGRAPHIC AREAS

(71) Applicant: Walmart Apollo, LLC, Bentonville, AR (US)

(72) Inventors: Bryant J. Woolsey, Centerton, AR (US); Lewis B. Johnson, Austin, TX (US); Jenna R. Ackerman, Chicago, IL (US)

(73) Assignee: Walmart Apollo, LLC, Bentonville, AR (US)

( * ) Notice: Subject to any disclaimer, the term of this patent is extended or adjusted under 35 U.S.C. 154(b) by 462 days.

(21) Appl. No.: 17/552,314

(22) Filed: Dec. 15, 2021

(65) Prior Publication Data

US 2022/0189593 A1    Jun. 16, 2022

Related U.S. Application Data

(60) Provisional application No. 63/125,584, filed on Dec. 15, 2020.

(51) Int. Cl.
*G16H 40/20* (2018.01)
*G16H 10/60* (2018.01)

(52) U.S. Cl.
CPC .............. *G16H 10/60* (2018.01); *G16H 40/20* (2018.01)

(58) Field of Classification Search
CPC ................................ G16H 40/20; G16H 10/60
See application file for complete search history.

(56) References Cited

U.S. PATENT DOCUMENTS

| | | | |
|---|---|---|---|
| 9,996,666 B1 * | 6/2018 | Wilson | G06F 16/9537 |
| 10,664,572 B2 * | 5/2020 | Bitran | G16H 20/60 |
| 11,282,041 B2 * | 3/2022 | Sanderford | G06Q 10/1095 |

(Continued)

OTHER PUBLICATIONS

Institute of Medicine (US) Committee for the Study of the Future of Public Health. The Future of Public Health. Washington (DC): National Academies Press (US); 1988. 6, Conclusions and Recommendations. Available from: https://www.ncbi.nlm.nih.gov/books/NBK218216/ (Year: 1988).*

*Primary Examiner* — Joshua B Blanchette
(74) *Attorney, Agent, or Firm* — Fitch, Even, Tabin & Flannery, LLP

(57) ABSTRACT

Systems and methods for estimating a net health visit demand of potential patients located in one or more geographic areas include one or more electronic databases that store electronic information associated with the potential patients, health care service providers, and general health visit recommendations for the potential patients. A computing device in communication with the database includes a control circuit configured to calculate an estimated total number of health care visits recommended for the potential patients located in a geographic area within a window of time, and to calculate an estimated total number of health care visits that the health care service providers located in the geographic area can accommodate within the window of time. Based on correlating these numbers, the control circuit generates an output indicating whether the health care visit capacity of health care service providers in the selected geographic area is suggested to be increased or reduced.

16 Claims, 9 Drawing Sheets

(56) References Cited

U.S. PATENT DOCUMENTS

2020/0258054 A1\* 8/2020 Kaufman ........... G06Q 10/1095
2022/0384003 A1\* 12/2022 Gnanasambandam ......................
                                                              G16H 10/60

\* cited by examiner

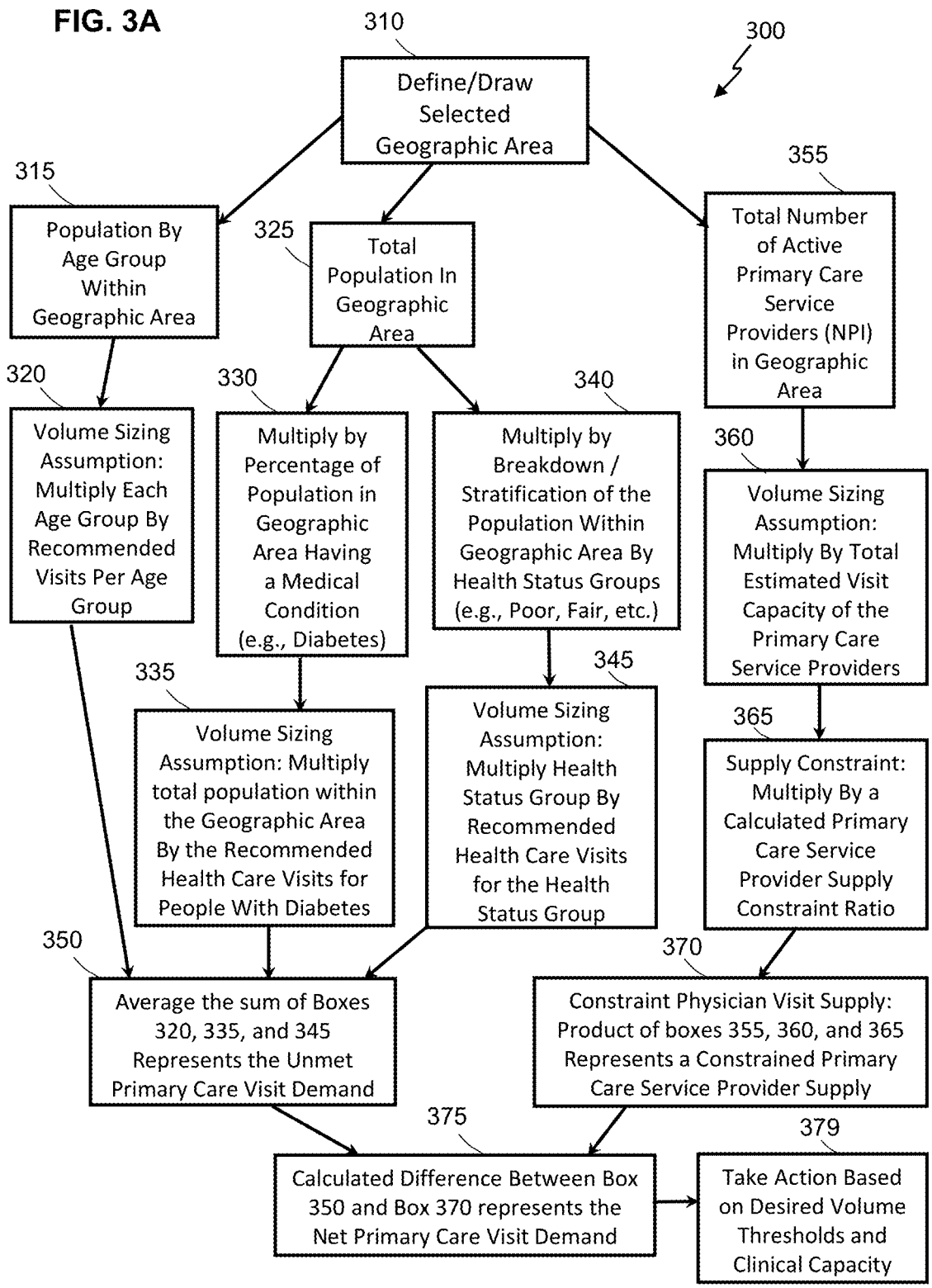

FIG. 5A

| Store Number | Geographic Area of Interest | Net Primary Care Visit Demand |
|---|---|---|
| 1 | 401 | -13,983 (L) |
| 2 | 402 | -88,673 (L) |
| 3 | 403 | 83,184 (H) |
| 4 | 404 | -21,972 (L) |
| 5 | 405 | 16,418 (M) |
| 6 | 406 | 9,738 (M) |
| 7 | 407 | -1,444 (L) |
| 8 | 408 | 24,525 (M) |
| 9 | 409 | 113,323 (H) |
| 10 | 410 | 45,399 (H) |

FIG. 5B

Recommendation

- Build: Yes (90% probability)
- Health Care Model:
  - Primary Care (95%)
  - Dental Care (60%)
  - Vision Care (80%)
  - Emergency (95%)
- Financial Health: Excellent

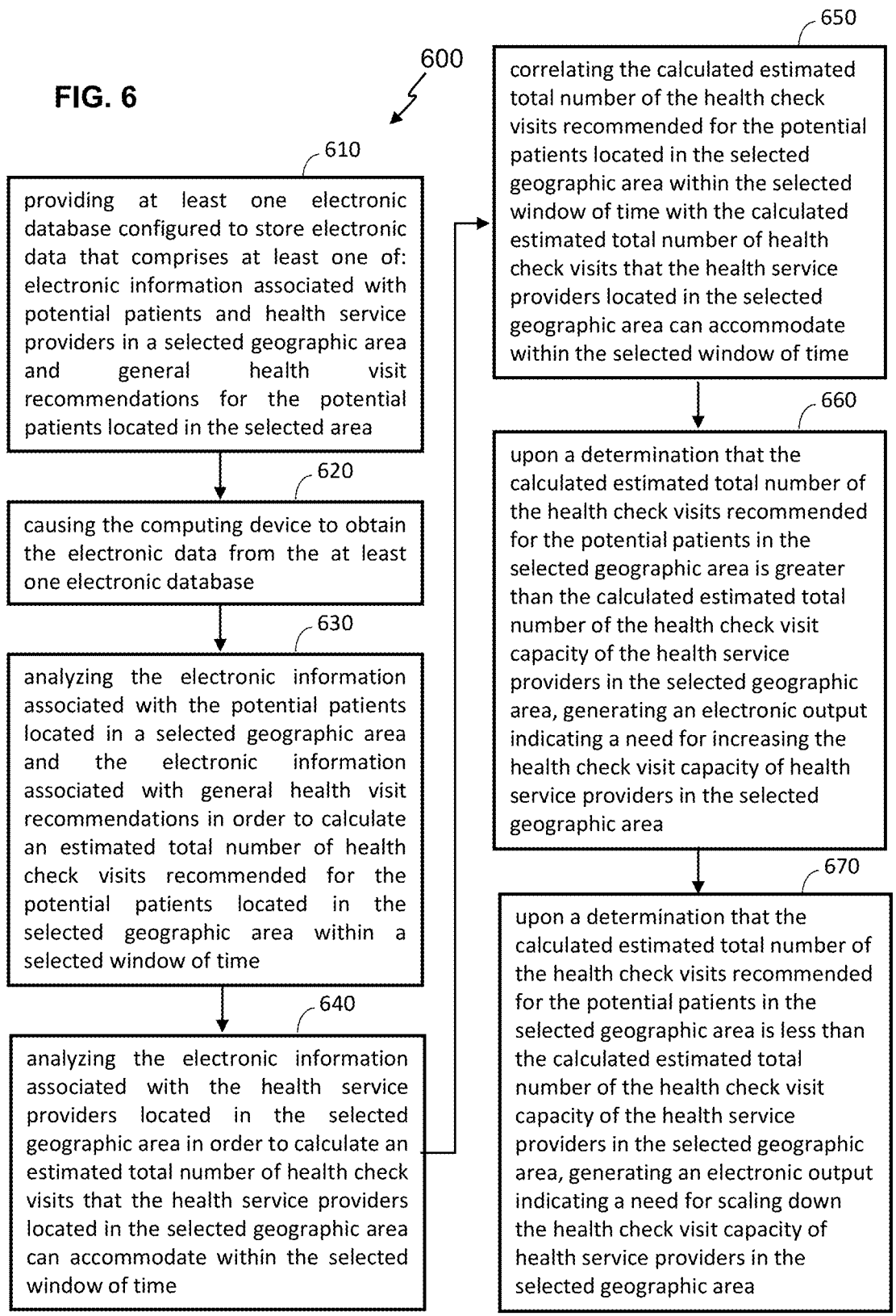

SYSTEMS AND METHODS FOR ESTIMATING A NET HEALTH CARE DEMAND OF POTENTIAL PATIENTS IN ONE OR MORE GEOGRAPHIC AREAS

RELATED APPLICATIONS

This application claims the benefit of U.S. Provisional Application No. 63/125,584, filed Dec. 15, 2020, which is incorporated herein by reference in its entirety.

TECHNICAL FIELD

This invention relates generally to evaluating heath care service provider availability in geographic areas and, in particular, to estimating a net health care visit demand of potential patients located in one or more geographic areas.

BACKGROUND

Most of the large retailers do not simply offer their customers retail products for sale, but also offer services not typically associated with retail stores, for example, pharmacy and optometry services. Some of the large retailers may be actively offering or contemplating to offer medical care services and/or dental care services as well. Given that a typical large retailer has thousands of stores spread across a large geographic area, and since some stores are located in more densely populated (e.g., urban) geographic areas and some stores are located in less populated (e.g., rural) geographic areas, the health visit demand by the customers of the retailer may greatly fluctuate from store to store.

The staffing needs of a medical care provider (e.g., the number of physicians, nurses, etc.) and/or a dental services provider (e.g., the number of dentists, hygienists, etc.) that may be operated by a large retailer are likely to be determined by the anticipated medical/dental visit demand of the current and/or future customers of the retailer in a given geographic area surrounding a given retail facility location of the retailer. Accordingly, there is a need for a system that can automatically determine the net health (i.e., medical, dental, etc.) visit demand of potential patients in that geographic area.

BRIEF DESCRIPTION OF THE DRAWINGS

Disclosed herein are embodiments of systems, apparatuses, and methods pertaining to estimating a net health visit demand of potential patients located in one or more geographic areas. This description includes drawings, wherein:

FIG. 3A is a diagram representing an overview flow chart of an exemplary process of estimating a net primary health care visit demand of potential patients located in one or more geographic areas in accordance with some embodiments.

FIG. 5A is an exemplary screenshot illustrating the calculated estimated net health visit demand at multiple geographic locations and generated on a display screen of the computing device of FIG. 2.

FIG. 5B is an exemplary screenshot illustrating an exemplary output by the computing device that relates to increasing various health care service operations in an exemplary geographic area analyzed by the computing device of FIG. 2.

FIG. 6 is a flow chart diagram of a method of estimating a net health care visit demand of potential patients located in one or more geographic areas in accordance with some embodiments in accordance with some embodiments.

Figure 1:
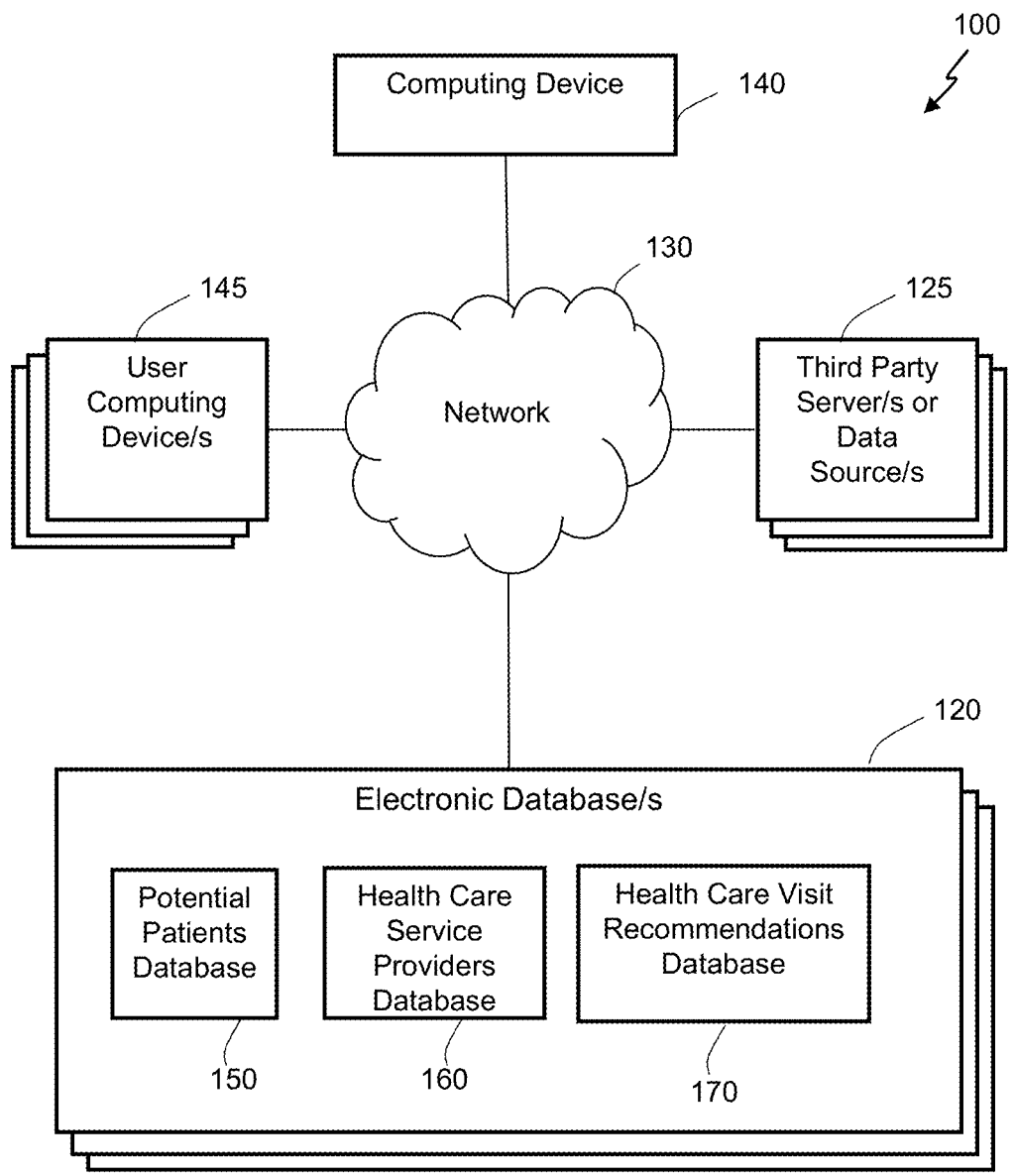
FIG. 1 is a diagram of a system of estimating a net health care visit demand of potential patients located in one or more geographic areas in accordance with some embodiments.

Elements in the figures are illustrated for simplicity and clarity and have not been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

The following description is not to be taken in a limiting sense, but is made merely for the purpose of describing the general principles of exemplary embodiments. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Generally speaking, this disclosure relates to systems and methods for estimating a net health care visit demand of potential patients located in one or more geographic areas, which include one or more electronic databases that store electronic information associated with the potential patients, health care service providers, and general health care visit recommendations for the potential patients. A computing device in communication with the database includes a control circuit configured to calculate: an estimated total number of health care visits recommended for the potential patients located in a selected geographic area within a selected window of time; and an estimated total number of health care visits that the health care service providers located in the selected geographic area can accommodate within the selected window of time. The control circuit correlates these numbers and, based on the correlation, generates an electronic output indicating whether the health care visit capacity of health care service providers in the selected geographic area needs to be increased or reduced.

In some embodiments, a system for estimating a net health care demand of potential patients located in one or more geographic areas includes at least one electronic database configured to store electronic data. The electronic database comprises at least one of: electronic information associated with the potential patients located in a selected geographic area; electronic information associated with health care service providers located in the selected geographic area; and electronic information associated with general health care visit recommendations for the potential patients located in the selected geographic area. The system further includes a computing device including a control circuit having a programmable processor. The control circuit configured to: cause the computing device to obtain the electronic data from the at least one electronic database, analyze the electronic information associated with the potential patients located in a selected geographic area and the electronic information associated with general health care visit recommendations in order to calculate an estimated total number of health care visits recommended for the potential patients located in the selected geographic area within a selected window of time; analyze the electronic information associated with the health care service providers located in the selected geographic area in order to calculate an estimated total number of health care visits that the health care service providers located in the selected geographic area can accommodate within the selected window of time; and correlate the calculated estimated total number of the health care visits recommended for the potential patients located in the selected geographic area within the selected window of time with the calculated estimated total number of health care visits that the health care service providers located in the selected geographic area can accommodate within the selected window of time. Upon a determination by the control circuit that the calculated estimated total number of the health care visits recommended for the potential patients in the selected geographic area within the selected window of time is greater than the calculated estimated total number of the health care visits that the health care service providers in the selected geographic area can accommodate within the selected window of time, generate an electronic output, indicating a need for increasing the health care visit capacity of health care service providers in the selected geographic area. Upon a determination by the control circuit that the calculated estimated total number of the health care visits recommended for the potential patients in the selected geographic area within the selected window of time is less than the calculated estimated total number of the health care visits that the health care service providers in the selected geographic area can accommodate within the selected window of time, generate an electronic output, indicating a need for reduction of the health care visit capacity of health care service providers in the selected geographic area.

In some embodiments, a method of estimating a net health care demand of potential patients located in one or more geographic areas includes providing at least one electronic database configured to store electronic data that comprises at least one of: electronic information associated with the potential patients located in a selected geographic area; electronic information associated with health care service providers located in the selected geographic area; and electronic information associated with general health visit recommendations for the potential patients located in the selected geographic area. The method further includes providing a computing device including a control circuit having a programmable processor, and, by the control circuit: causing the computing device to obtain the electronic data from the at least one electronic database; analyzing the electronic information associated with the potential patients located in a selected geographic area and the electronic information associated with general health visit recommendations in order to calculate an estimated total number of health care visits recommended for the potential patients located in the selected geographic area within a selected window of time; analyzing the electronic information associated with the health care service providers located in the selected geographic area in order to calculate an estimated total number of health care visits that the health care service providers located in the selected geographic area can accommodate within the selected window of time; correlating the calculated estimated total number of the health care visits recommended for the potential patients located in the selected geographic area within the selected window of time with the calculated estimated total number of health care visits that the health care service providers located in the selected geographic area can accommodate within the selected window of time. Upon a determination by the control circuit that the calculated estimated total number of the health care visits recommended for the potential patients in the selected geographic area within the selected window of time is greater than the calculated estimated total number of the health care visits that the health care service providers in the selected geographic area can accommodate within the selected window of time, the method further includes generating an electronic output indicating a need for increasing the health care visit capacity of health care service providers in the selected geographic area. Upon a determination by the control circuit that the calculated estimated total number of the health care visits recommended for the potential patients in the selected geographic area within the selected window of time is less than the calculated estimated total number of the health care visits that the health care service providers in the selected geographic area can accommodate within the selected window of time, the method further includes generating an electronic output indicating a need for reduction of the health care visit capacity of health care service providers in the selected geographic area.

FIG. 1 illustrates one embodiment of a system 100 of estimating a net health visit demand of potential patients located in one or more selected geographic areas. In some embodiments, a selected geographic area may include a facility of a retailer, which may be a large retail store that includes one or more departments/offices that offer health care service providers to the customers of the retailer. In some aspects, the health care service providers that provide health services on behalf of the retailer may be deployed in an office location or a modular health services clinic that is not incorporated into the physical structure of a store/supercenter operated by the retailer.

The exemplary system 100 depicted in FIG. 1 includes an electronic database 120, which may be one electronic database, or a collection of separate and distinct databases that may be interconnected or independently accessible by one or more computing devices. The electronic database 120 may be stored, for example, on non-volatile storage media (e.g., a hard drive, flash drive, or removable optical disk) internal or external relative to the computing device 140 (which will be described in more detail below), or internal to computing devices separate and distinct from the computing device 140.

In some embodiments, the electronic database 120 stores electronic data that comprises electronic information associated with the potential patients located in the selected geographic area and at least one geographic area adjacent the selected geographic area; electronic information associated with health care service providers located in the selected geographic area; and electronic information associated with general health visit recommendations for the potential patients located in the selected geographic area. For example, to that end, an exemplary electronic database 120 depicted in FIG. 1 includes (and/or is in communication with) a potential patient database 150, a health care service provider database 160, and a health visit recommendation database 170. It will be appreciated that the electronic database 120 may include many other electronic databases than the exemplary databases depicted in FIG. 1.

In some embodiments, in addition to the electronic databases 120, 150, 160, and 170, which may be operated by/for the retailer, the exemplary system 100 may include data sources such as one or more third party servers 125 (e.g., servers operated by various third parties relative to the retailer, for example, public and private organizations that specialize in health data accumulation and/or analytics). In certain implementations, the computing device 140 may obtain certain data over the network 130 from the third-party servers 125, and to transmit this data for storage to the electronic database 120 (i.e., one or more of the sub-databases 150, 160, and 170).

The system 100 includes a computing device 140 that is generally configured to obtain electronic data from the electronic database 120, and to process the data according to pre-programmed algorithms and/or business rules in order to arrive at a decision of whether the capacity of health care service providers to accommodate health care visits (e.g., medical visits, dental visits, etc.) in the selected geographic area needs to be increased or reduced. The computing device 140 shown in FIG. 1 may be a stationary, portable, or hand-held electronic device (or a combination of one or more such devices), for example, a desktop computer, a laptop computer, a tablet, a mobile phone, or any other device that may be configured for data entry and communication with another device located at a facility operated by or for the retailer (e.g., a regional server configured for two-way communication with the electronic database 120).

In the embodiment illustrated in FIG. 1, the computing device 140 is configured to communicate with various electronic devices (e.g., electronic database 120, potential patient database 150, a health care service provider database 160, health visit recommendation database 170, portable electronic device of a worker at a retailer facility, etc.) via a network 130. The exemplary network 130 depicted in FIG. 1 may be a wide-area network (WAN), a local area network (LAN), a personal area network (PAN), a wireless local area network (WLAN), or any other internet or intranet network, or combinations of such networks. Generally, communication between various electronic devices of system 100 may take place over hard-wired, wireless, cellular, Wi-Fi or Bluetooth networked components or the like. In some embodiments, one or more electronic devices of system 100 may include cloud-based features, such as cloud-based memory storage.

The system 100 includes one or more user computing device 145 that are generally configured for two-way communication over the network 130 with the computing device 140 and/or the electronic database 120. The user computing device/s 145 may be stationary, portable, or hand-held electronic device/s (or a combination of one or more such devices), for example, a desktop computer, a laptop computer, a tablet, a mobile phone, or any other device that may be configured for data entry and communication with other electronic devices over the network 130. In some implementations, the user computing devices 145 may be configured for receiving electronic communications/alerts (e.g., by way of text message, electronic-email, web-based interface, mobile app., etc.) from the computing device 140, and, in response to these electronic communications/alerts, to generate a graphical interface on the display screen of the user computing device 145, which may provide an informational notification/alert to the user and/or may require the user to perform one or more tasks in response to the received alert. In some aspects, the graphical interface generated on the display screen of the user computing device 145 may be interactive in that it permits the user of the computing device 145 to enter a response or to indicate that a task has been performed.

Figure 2:
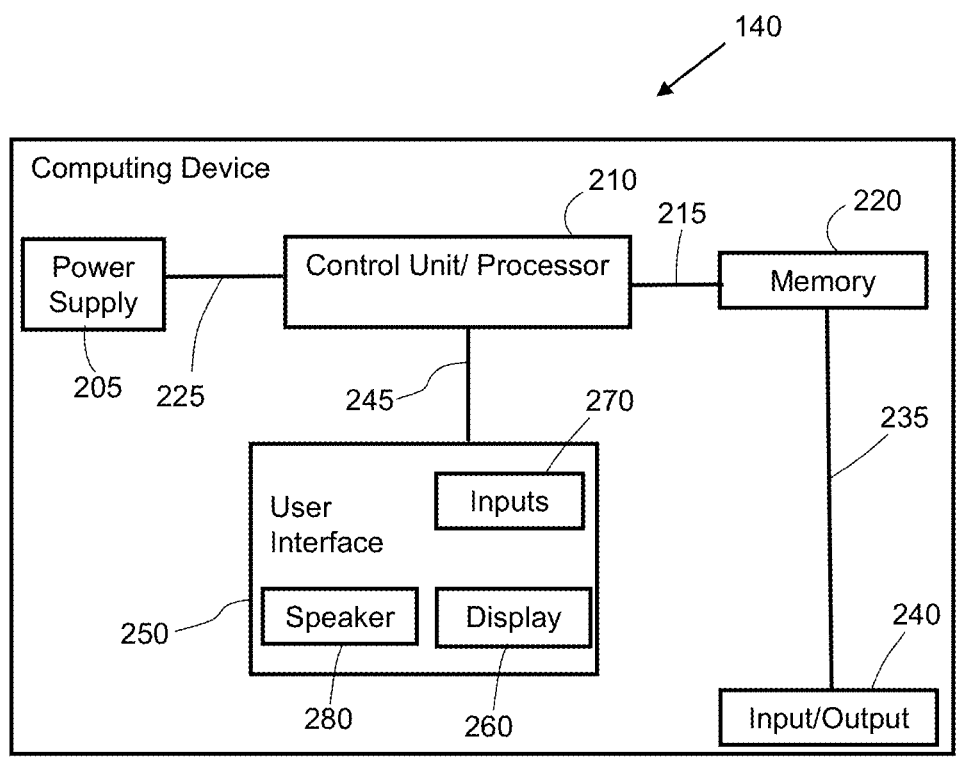
FIG. 2 is a functional diagram of the computing device of FIG. 1 in accordance with several embodiments.

With reference to FIG. 2, an exemplary computing device 140 configured for use with exemplary systems and methods described herein may include a control circuit or control unit 210 including a processor (for example, a microprocessor or a microcontroller) electrically coupled via a connection 215 to a memory 220 and via a connection 225 to a power supply 205. The control circuit 210 can comprise a fixed-purpose hard-wired platform or can comprise a partially or wholly programmable platform, such as a microcontroller, an application specification integrated circuit, a field programmable gate array, and so on. These architectural options are well known and understood in the art and require no further description here.

This control circuit 210 can be configured (for example, by using corresponding programming stored in the memory 220 as will be well understood by those skilled in the art) to carry out one or more of the steps, actions, and/or functions described herein. In some embodiments, the memory 220 may be integral to the processor-based control circuit 210 or can be physically discrete (in whole or in part) from the control circuit 210 and is configured non-transitorily store the computer instructions that, when executed by the control circuit 210, cause the control circuit 210 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM)) as well as volatile memory (such as an erasable programmable read-only memory (EPROM))). Accordingly, the memory and/or the control unit may be referred to as a non-transitory medium or non-transitory computer readable medium.

The control circuit 210 of the computing device 140 is also electrically coupled via a connection 235 to an input/output 240 that can receive signals from the computing device 140, or from any other source that can communicate with the computing device 140 via the network 130. The input/output 240 of the computing device 140 can also send signals to the electronic database 120 and/or to any other device in wired or wireless communication with the computing device 140 over the network 130 or any other communication channel.

In the embodiment shown in FIG. 2, the processor-based control circuit 210 of the computing device 140 is electrically coupled via a connection 245 to a user interface 250, which may include a visual display or display screen 260 (e.g., light-emitting-diode (LED) screen) and/or button input 270 that provide the user interface 250 with the ability to permit an operator of the computing device 140 to manually control the computing device 140 by inputting commands via touch-screen and/or button operation and/or voice commands. In some embodiments, the user interface 250 of the computing device 150 may also include a speaker 280 that provides audible feedback (e.g., alerts) to the operator of the computing device 140. It will be appreciated that the performance of such functions by the processor-based control circuit 210 of the computing device 140 is not dependent on a human operator, and that the control circuit 210 may be programmed to perform such functions without a human operator.

In some embodiments, the display screen 260 of the computing device 140 is configured to display various graphical interface-based menus, options, and/or alerts that may be transmitted from the computing device 140 to, and displayed on, the computing device 140 in connection with various aspects of estimating a net health care demand of potential patients in one or more geographic areas. The inputs 270 of the computing device 140 may be configured to permit an operator to navigate through the on-screen menus on the computing device 140 and make changes and/or updates to the analytical models by way of which the control circuit 210 estimates the net health care demand. It will be appreciated that the display screen 260 may be configured as both a display screen and an input 270 (e.g., a touchscreen that permits an operator to press on the display screen 260 to enter text and/or execute commands.)

In the exemplary embodiment illustrated in FIG. 1, the electronic database 120 includes or is coupled to a potential patient database 150. In some aspects, the potential patient database 150 may store electronic data relating to the potential patients located in one or more geographic areas, whose net health care visit demand can be analyzed and estimated by the control circuit 210 of the computing device 140 (which will be described in more detail below). In some embodiments, the potential patient database 150 stores electronic data representing a profile of each of the potential patients. In certain aspects, the profile of each of the potential patients includes a physical address of the potential patient (which may be a home address and/or a work address), age of the potential patients, an indication of whether each of the potential patients is (or is not) a current/previous customer of the retailer, health-related conditions of the potential patients (which may be derived from, for example, Census data, Esri, Experian, etc.), general health status of the potential patients (which may be derived from Census Data, for example), insurance information of the potential patients (which may be derived from private and/or city/state/federal government-based sources), etc.

The exemplary electronic database 120 of FIG. 1 further includes or is coupled to a health care service provider database 160. In some aspects, the health care service provider database 160 stores electronic data relating to the health care service providers located in one or more geographic areas, who are active in taking in and treating patients, and whose health care visit availability/capacity can be analyzed and estimated by the control circuit 210 of the computing device 140 (which will be described in more detail below). In some embodiments, the health care service provider database 160 may store electronic data representing a physical addresses of each of the health care service providers, operating hours of the health care service providers, a total number of doctors associated with each of the health care service providers, a total number of physician assistants and/or dental hygienists associated with each of the health care service providers, claims submitted for processing/payment by the health care service providers, etc. In some embodiments, the health care service provider database 160 includes data and analytics obtained from one or more available online sources, for example PerceptionHealth® (which may provide the retailer, inter alia, with medical claims data associated with the medical/dental service providers).

The exemplary electronic database 120 of FIG. 1 further includes or is coupled to a health visit recommendation database 170. In some aspects, the health visit recommendation database 170 stores electronic data relating to the number of visits recommended by various health organizations/associations for the potential patients. In some embodiments, the health visit recommendation database 170 may include websites/servers of various city, state, federal health organizations (e.g., Center for Disease Control and Prevention, National Institute of Health, state-owned universities, etc.), or private health organizations (e.g., American Medical Association, American Dental Association, County Health Rankings & Roadmaps, private universities, etc.), where these organizations post suggested guidance as to how many times a year a person of a given age group (e.g., 0-10, 30-40, 60-70, etc.) and/or how many times a year a person with given health status (poor, fair, good, very good, excellent, etc.) and/or medical condition (e.g., gingivitis, gum disease, diabetes, cardiovascular disease, chronic kidney disease, chronic liver disease, cancer, etc.) should visit a health care service provider to maintain optimal health.

As will be described in more detail below, in some embodiments, the control circuit 210 of the computing device 140 is programmed to cause the computing device 140 to obtain electronic data from the electronic database 120 over the network 130 and to analyze the electronic data obtained by the computing device 140 from the electronic database 120 in order to determine whether the health care visit capacity of health care service providers in the selected geographic area needs to be increased or reduced. For example, in some aspects, the control circuit 210 of the computing device 140 is programmed to analyze the electronic information associated with the potential patients located in a selected geographic area (which is obtained by the computing device 140 from the electronic database 120) and the electronic information associated with general health visit recommendations (which is obtained by the computing device 140 from the electronic database 120) in order to calculate an estimated total number of health care visits recommended for the potential patients located in the selected geographic area within a selected window of time. In other aspects, the control circuit 210 of the computing device 140 is programmed to analyze the electronic information associated with the health care service providers located in the selected geographic area (which is obtained by the computing device 140 from the electronic database 120) in order to calculate an estimated total number of health care visits that the health care service providers located in the selected geographic area can accommodate within this window of time.

As mentioned above, the control circuit 210 of the computing device 140 is programmed to determine whether the health care visit capacity of health care service providers in the selected geographic area needs to be increased or reduced. To that end, in some implementations, the control circuit 210 of the computing device 140 is programmed to correlate (1) the calculated estimated total number of the health care visits recommended for the potential patients located in the selected geographic area within the selected window of time and (2) the calculated estimated total number of health care visits that the health care service providers located in the selected geographic area can accommodate within the selected window of time. In one aspect, this correlation is a comparison of these two numbers to determine which number is larger and which number is smaller.

In some embodiments, when the control circuit 210 of the computing device 140 determines (based on the above-described correlation) that the calculated estimated total number of the health care visits recommended for the potential patients in the selected geographic area within the selected window of time is greater than the calculated estimated total number of the health care visits that the health care service providers in the selected geographic area can accommodate within the selected window of time, the control circuit 210 is programmed to generate an electronic output, indicating a need for increasing the health care visit capacity of health care service providers in the selected geographic area. On the other hand, when the control circuit 210 of the computing device 140 determines (based on the above-described correlation) that the calculated estimated total number of the health care visits recommended for the potential patients in the selected geographic area within the selected window of time is less than the calculated estimated total number of the health care visits that the health care service providers in the selected geographic area can accommodate within the selected window of time, the control circuit 210 is programmed to generate an electronic output, indicating a need for reducing the health care visit capacity of health care service providers in the selected geographic area.

In some aspects, the processor of the control circuit 210 is programmed to generate a signal that is configured to generate, on the electronic display 260 of the computing device 140, a graphical interface including an indication of the net health care visit demand of the potential patients in one or more selected geographic areas analyzed by the control circuit 210 of the computing device 140. These functions of the control circuit 210 of the computing device 140 will be described in more detail below. As mentioned above, these outputs of the control circuit 210 that are generated by the control circuit 210 of the computing device 140 may be transmitted by the computing device to one or more user computing device 145 to generate a graphical interface on the display screen of the user computing device 145, which may provide an informational notification/alert to the user of the user computing device 145 and/or may require the user of the user computing device 145 to perform one or more tasks in response to the alert.

An overview of an exemplary workflow associated with a determination of the net primary (medical) care visit demand of the potential patients in one or more geographic areas is depicted in FIG. 3A. At the outset of the exemplary workflow 300 depicted in FIG., the control circuit 210 of the computing device 140 defines/draws a selected geographic area to be analyzed for net primary care visit demand by the control circuit 210 (step 310). In some embodiments, the control circuit 210 is programmed to define the selected geographic area as a perimeter that is estimated by the control circuit 210 to be within a driving time corresponding to a predetermined number of minutes (e.g., 15, 30, 45, 60, etc.) from a center of the selected geographic area.

The driving time from a center to a perimeter of a given geographic area may be estimated by the control circuit 210 based on urbanicity drive time data and/or mass mobile drive time data. The selected drive time for defining the perimeter of the selected geographic area may be drive time in a private car, or drive time in public transportation. In some embodiments, the control circuit 210 is programmed to define the selected geographic area as a perimeter/circumference that is estimated by the control circuit 210 to have a predetermined radius (e.g., 3, miles, 5 miles, 10 miles, 15 miles, etc.).

Figure 4A:
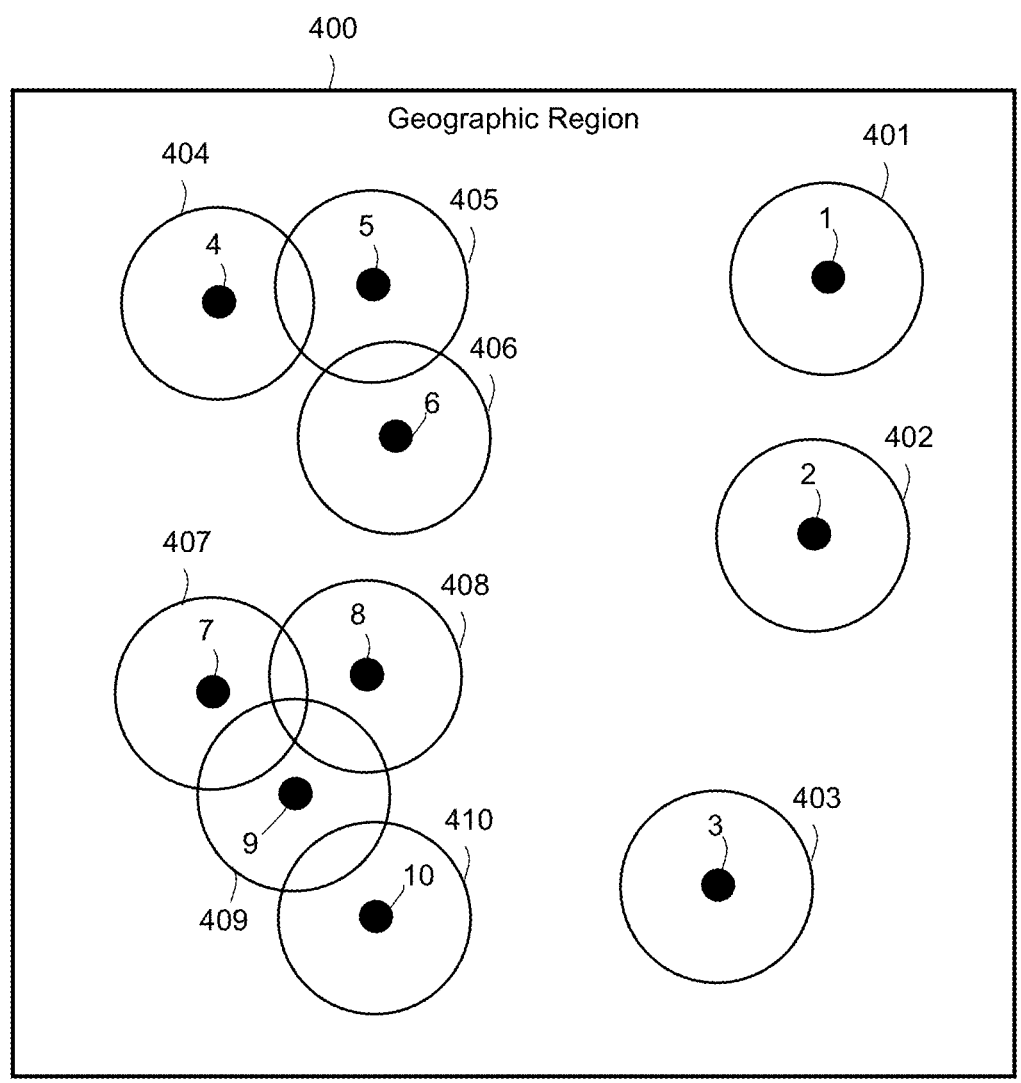
FIG. 4A is a diagram representing a sample geographic region including multiple exemplary geographic areas, which may be analyzed by the computing device of FIG. 2 for health care visit demand by potential patients.

An exemplary geographic region 400 containing multiple geographic areas 401-410 selected by the control circuit 210 of the computing device 140 for analysis is depicted in FIG. 4A. As can be seen in FIG. 4A, some of the geographic areas may be non-overlapping (e.g., geographic areas 401, 402, and 403), some geographic areas may overlap only one other geographic area (e.g., geographic areas 404, 406, and 410), some geographic areas may overlap two other geographic areas (e.g., geographic areas 405, 407, and 408), and some geographic areas may overlap three other geographic areas (e.g., geographic area 409). In will be appreciated that each of the geographic areas 401-410 shown in FIG. 4A may overlap more four or more geographic areas as well. and In FIG. 4A, a facility 1-10 of the retailer (e.g., a retail store including health service departments/offices, a stand-alone health care service provider location, etc.) is located at the center of each of the geographic areas 401-410. It will be appreciated that the control circuit 210 can be programmed to analyze the net health care visit demand in any geographic area, whether it includes an active facility of the retailer or not, and whether the facility of the retailer is located at the center of the geographic area or off center in the geographic area.

Figure 4B:
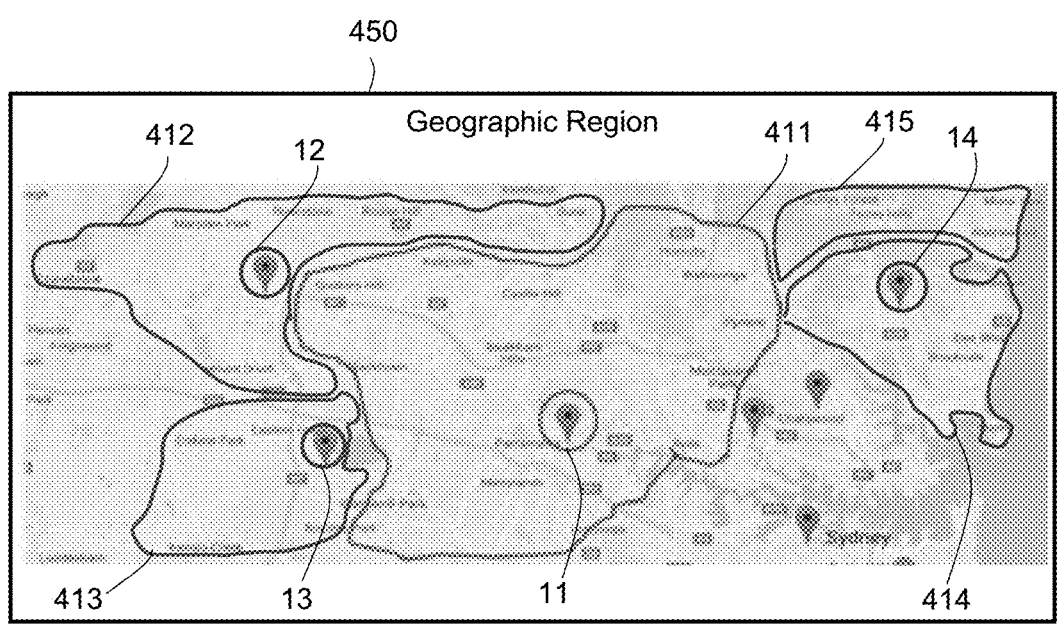
FIG. 4B is a diagram representing a sample geographic region including an exemplary irregularly shaped geographic area, which may be analyzed by the computing device of FIG. 2 for health care visit demand by potential patients.

Notably, while the exemplary selected geographic areas 401-410 are depicted in FIG. 4A as circles, it will be appreciated that the selected geographic areas 401-410 may be of any regular geometric shape (rectangular, trapezoidal, triangular, trapezoidal, etc.), or may have an irregular shape matching the shape of any geographic area of business interest for the retailer. In particular, FIG. 4B illustrates an exemplary geographic region 450 containing several exemplary geographic areas (411, 412, 413, and 414), each having an irregular shape. As shown in FIG. 4B, the exemplary geographic areas 411, 412, 413, and 414 where the control circuit 210 of the computing device 140 may analyze/estimate the unmet health care demand each include one facility (e.g., store supercenters 11, 12, 13, 14) of the retailer, and that neither of the retail facilities 11, 12, 13, and 14 are located at the center of the irregularly-shaped geographic areas 411, 412, 413, and 414. FIG. 4B also shows that the control circuit 210 of the computing device 140 may be programmed to analyze/estimate the unmet health care demand in an irregularly-shaped geographic area 415 that does not (yet) include a facility operated by the retailer (and represents an opportunity for expansion by the retailer).

Figure 4C:
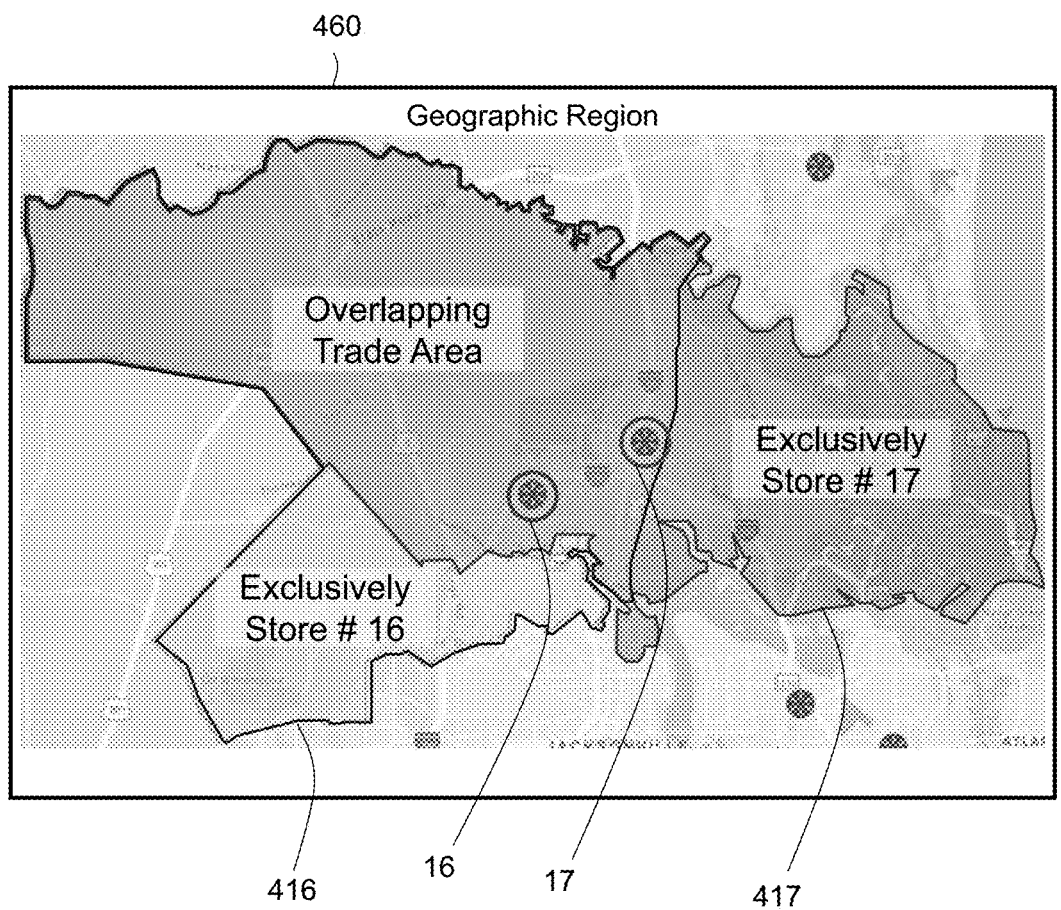
FIG. 4C is a diagram representing a sample geographic region including two exemplary irregularly shaped overlapping geographic areas, which may be analyzed by the computing device of FIG. 2 for health care visit demand by potential patients.

FIG. 4C illustrates another exemplary geographic region 460, which was analyzed by the control circuit 210, with the result being that the control circuit 210 generated two irregularly shaped overlapping geographic areas of interest for analyzing the health care demand. In FIG. 4C, the geographic area 416 includes a portion that contains the physical address of the potential patients that are expected (based on analysis by the control circuit 210) to drive only to retail facility 416 instead of retail facility 417 when they go in for a health care visit. Similarly, the geographic area 417 includes a portion that contains the physical address of the potential patients that are expected (based on analysis by the control circuit 210) to drive only to retail facility 417 instead of retail facility 416 when they go in for a health care visit. In addition, FIG. 4C illustrates that geographic areas 416 and 417 overlap, such that the overlapping portions of geographic areas 416 and 417 contain the physical address of the potential patients that are expected (based on analysis by the control circuit 210) to drive to either retail facility 416 or retail facility 417 when they go in for a health care visit. In some embodiments, to protect the privacy of the population living within the geographic region 460, the electronic database 140 stores physical addresses of potential patients that reside within a geographic area (e.g., 416 and 417 in FIG. 4C) without associating the physical addresses with the identity of the person(s) residing at those physical addresses. As such, in certain implementations, the control circuit 210 may obtain physical address information from the electronic database 140 without obtaining any data associating the physical address information with the identity of the people residing at the address.

In some embodiments, the control circuit 210 is programmed to define the geographic area of interest while taking into account various factors associated with the geographic area, including but not limited to, population density, traffic constraints, travel obstacles, etc. These factors may be obtained and/or analyzed via data accumulation and/or analytic tools (e.g., Alteryx). Notably, the shape of the geographic areas 401-410 in FIG. 4A and the geographic areas 411-415 in FIG. 4B may be defined by the control circuit 210 based on one or more business rules programmed into the control circuit 210, or may be defined by a user (e.g., national/regional/local manager of the retailer) of the computing device 140.

In some embodiments, the control circuit 210 is programmed to perform the following actions during the process of determining a geographic area for health care demand analysis. First, the control circuit 210 is programmed to define a geographic area of interest for analyzing the health care demand of potential patients by first defining a location of interest (state, core-based statistical area (cbsa), coordinates (e.g., latitude/longitude), etc.). After selecting a given geographic area of interest, the control circuit 210 is programmed to evaluate the movement behavior of the population relative to retail/convenience transactions (in-store retail purchases, internet-based retail purchases, etc.). In addition, the control circuit 210 is programmed to evaluate the movement behavior of the population relative to retail/convenience relative to healthcare service transactions (e.g., medical office visits, dental office visits, etc.) Further, the control circuit 210 is programmed to evaluate population movement behavior relative to a dwelling (i.e., residence address-based evaluation) and/or employment (i.e., business address-based evaluation). The control circuit 210 would then develop the boundaries defining the geographic area of interest based on analysis/evaluations of the factors described in this paragraph.

In some implementations, to create/draw the boundaries of a geographic area of analytical interest, the control circuit 210 is programmed to evaluate the medical care visit counts (e.g., extrapolated from mass mobile data analysis) between the area of interest and the retail, healthcare, employment, and residential locations within the area of interest at a predetermined/preset group level. In some embodiments, the control circuit 210 may be programmed to evaluate urbanicity data (e.g., population concentrations and associated travel time across a given geographic area through those concentrations). In some embodiments, the control circuit 210 may also be programmed to evaluate data pertaining to health industry standards for medical facility placement, when determining the overall shape of a given geographic area.

In some embodiments, the control circuit 210 employs mass mobile data analysis for this purpose. For example, if a mobile device of each person living in a given geographic area is set up to send a ping to a mobile device location monitoring service when the person is at home/at work and when the person is at a supercenter/modular health care office of the retailer, the control circuit 210 can obtain this data, and determine the health care locations visited more/less frequently by the people living/working in a given geographical area of interest. In some embodiments, to protect the privacy of the population living within the geographic region 460, the electronic signal including the ping sent from the mobile device of each person does not reveal the identity of the person who owns the mobile device. As such, in certain implementations, the control circuit 210 may obtain data that reveals current locations of the mobile devices of potential patients without associating these mobile devices with the identity of the owners of these devices.

In certain aspects, the control circuit 210 is programmed to analyze the obtained mass mobile data with respect to a population residing/working in a geographic area of interest and sort the obtained mass mobile data based on highest number of health care visits to lowest number of health care visits until the control circuit 210 accounts for a suitable/statistically significant percentage of all health care visits (e.g., 60% of total visits). In some embodiments, the control circuit 210 is programmed to then minimize/eliminate the outlier concentrations (e.g., from about 0 to about 5%) of the total health care visits of the people/population groups that that are located at a distance considered to be impractical for driving to a retail supercenter/health care provider location of interest.

Further, the control circuit 210 may be programmed to generate an outline of all of the other health care visit groups (that remain after the removal of the outlier groups) using one or more data tools available to the control circuit 210 to "dissolve" the inner borders of the polygon to create a single outer boundary, which would then surround/enclose the final geographic area of interest (e.g., 401-417) to be analyzed. One data tool that the control circuit 210 may be programmed to utilize for dissolving the inner borders of the polygon to create a single geographic area (e.g., area 416 or area 417 in FIG. 4C) may be Python's Geopandas Package.

The systems and methods described herein can be configured to comply with privacy requirements which may vary between jurisdictions. For example, before any recording, collection, capturing or processing of customer data, a "consent to capture" process may be implemented. In such a process, consent may be obtained, from the customer, via a registration process. Part of the registration process may be to ensure compliance with the appropriate privacy laws for the location where the service would be performed. The registration process may include certain notices and disclosures made to the customer prior to the customer giving consent. In other words, the exemplary systems and methods described herein provide for no unauthorized/unconsented to collection or processing of data of customers.

In some embodiments, after registration, and before collection or processing of customer/potential patient location data, the system verifies that the customer/potential patient as registered with the system and has provides the required consent for data (e.g., location data) collection. That is, the customer's registration status as having consented to the collection of the customer's data can be verified by the system prior to collecting any customer data. This verification can take place, for example, by the customer entering a PIN (Personal Identification Number), password, or other code into a keypad or keyboard; by the customer entering into a limited geofence location while carrying a fob, mobile device (such as a smartphone), or other RF transmitter, where the device has been configured to broadcast an authorization signal.

In some embodiments, once consent is verified, customer data (e.g., location data) can be captured, processed and used. Absent verification of consent, the customer data collection features of the system remain inactive. Once consent is verified, customer data collection features of the system may be activated. In some aspects, if the system detects that customer data was inadvertently collected from the customer prior to verification of that customer's consent to the data collection, such collected data is immediately deleted, not having been saved to disk.

In some embodiments, customer data captured as part of the verification process is handled and stored by a single party at a single location. In some aspects, where data must be transmitted to an offsite location for verification, certain disclosures prior to consent are required, and the customer data is encrypted. The hashing of the customer data received is a form of asymmetrical encryption which improves both data security and privacy, as well as reducing the amount of customer data which needs to be communicated.

As mentioned above, the control circuit 210 of the computing device 104 analyzes data obtained from one or more databases 150, 160, 170 to estimate a net health care visit demand by the potential patients (e.g., current customers of the retailer, people who are not customers of the retailer currently, but who could conceivably use the medical care/dental care services provided by the retailer). Generally, in some embodiments, the control circuit 210 estimates the unconstrained health care visit demand and the health care service provider supply, and then subtracts the health care service provider supply from the unconstrained health care visit demand to obtain the net health care visit demand. The unconstrained health care visit demand generally refers to the total number of health (medial and/or dental) care visits recommended for people located within a geographic area of interests and: (1) being within certain age groups (e.g., 30-40, 60-70, etc.): (2) having certain medical/dental conditions/disorders (e.g., diabetes, gum disease, etc.); (3) being classified within certain health status groups (e.g., Poor, Fair, Good, Excellent, etc.). The health care visit supply generally refers to the total number of health care service providers (e.g., physicians, dentists, physical assistants, dental hygienists, etc.) and/or the capacity of the health care service providers in the geographic area of interest (i.e., the total number of health care visits that the health care service providers located in the geographic area may accommodate within a selected window of time (e.g., one month, one quarter, one year, etc.). The net health care visit demand generally refers to the net health care visit (e.g., medical doctor visit, dental visit, etc.) need of the people residing in the geographic area of interest.

In the exemplary embodiment depicted in FIG. 3A, after the control circuit 210 of the computing device 140 defines a selected geographic area, where the net health care visit demand of the residents will be analyzed, the control circuit 210 is programmed to obtain electronic data from the electronic database 120 to facilitate this analysis. In step 315, the control circuit 210 obtains electronic data representing a breakdown of the potential patients in the selected geographic area by a plurality of age groups. This data may be obtained by the control circuit 210, for example, from the exemplary potential patient database 150 depicted in FIG. 1, which, as mentioned above, may include Census data and other data indicative of names, addresses, and/or ages of the people living in a given geographic area.

After obtaining the electronic data representing the age groups, the control circuit 210 is programmed to obtain the electronic data representing the number of recommended health care visits within a selected period of time (e.g., one month, one quarter, one year) per age group (step 320). This data may be obtained by the control circuit 210, for example, from the health visit recommendation database 170, which, as mentioned above, may include health recommendation data posted by various health organizations, both private and public (for example, data provided by/obtained from organizations such as the Health Resources & Services Administration (HRSA), etc.). After obtaining the electronic data representing the number of recommended health care visits per age group, the control circuit 210 in step 320 then factors in the volume sizing assumption by multiplying the total number of the potential patients in each of the age groups by the number of the health care visits recommended within the selected window of time for each one of the age groups to obtain a first total primary care visit demand number. By way of example, if the control circuit 210 determines that the relevant age groups in a given geographic area are 10-20, 20-30, 30-40, 40-50, and 50-60, and that each group has 10,000 people in it, and that the recommended number of primary care (i.e., medical doctor) visits for the 10-20 group is 1, for the 20-30 group is 1, for the 30-40 group is 2, for the 40-50 group is 2, and for the 50-60 group is 3, then the first total primary care visit demand number calculated by the control circuit 210 in step 320 is 10,000 *1+10,000*1+ 10,000*2+10,000*2+10,000*3=90,000 visits per year.

In some aspects, after the control circuit 210 of the computing device 140 defines a selected geographic area, where the net health care visit demand of the residents will be analyzed (step 310), the control circuit 210 is programmed to obtain electronic data from the electronic database 120 representing the total number of people (i.e., potential patients) that reside in the selected geographic area (step 325). This electronic data may be obtained by the control circuit 210 from the potential patient database 150. In one aspect (see step 330), the control circuit 210 then obtains electronic data representing a percentage of the population in the selected geographic area that have a given medical condition (e.g., diabetes). This electronic data may be obtained by the control circuit 210 from the health visit recommendation database 170 (which may include data provided by/obtained from informational sources such as CountyHealthRankings.org, etc.). After obtaining the electronic data representing the total number of people (i.e., potential patients) that reside in the selected geographic area, the control circuit 210 in step 330 also multiplies the total number of people residing in the geographic area by the percentage of the people having the predetermined medical condition (e.g., diabetes).

In step 335, the control circuit 210 is programmed to obtain electronic data from the electronic database 120 representing the total number of health care visits recommended within the selected window of time for the potential patients having the predetermined medical condition. This data may be obtained by the control circuit 210, for example, from the health visit recommendation database 170. After obtaining this data, the control circuit 210 is also programmed to in step 335 to factor in the volume sizing assumption and multiply the product obtained in step 330 by the total number of health care visits recommended within the selected window of time for the potential patients having the predetermined medical condition to obtain a second total primary care visit demand number. By way of example, if the control circuit 210 determines in step 325 that the total number of people residing in a given geographic area is 100,000 and then determines in step 330 that the percentage of population having diabetes is 10%, and then determines in step 335 that the number of recommended health care visits annually for people with diabetes is 3, then the second total primary care visit demand number calculated by the control circuit 210 (which indicates the health care visit demand of people with diabetes living in the selected geographic area) would be 100,000*0.10*3=30,000 visits within a selected period of time.

In some aspects, after the control circuit 210 of the computing device 140 defines a selected geographic area where the net health care visit demand of the residents will be analyzed (step 310) and obtains electronic data from the electronic database 120 representing the total number of potential patients that reside in the selected geographic area (step 325), the control circuit is further programmed to obtain (see step 340) electronic data indicating a breakdown of the potential patients located in the selected geographic area by a plurality of overall health status groups (e.g. Poor, Fair, Good, Excellent, etc.). This electronic data may be obtained by the control circuit 210 from the potential patient database 150. In one aspect, the control circuit 210 in step 340 also multiplies the total number of the potential patients in each of the health status groups by the percentage of the potential patients located in the selected geographic area and classified in each of the health status groups.

In step 345, the control circuit 210 is programmed to obtain electronic data from the electronic database 120 representing the total number of primary care health care visits recommended within the selected window of time for the potential patients in each of the health status groups. This data may be obtained by the control circuit 210, e.g., from the health visit recommendation database 170. After obtaining this data, the control circuit 210 is also programmed to in step 345 to factor in the volume sizing assumption and multiply the product obtained in step 340 by the total number of primary care health care visits recommended within the selected window of time for the potential patients classified in each of the health status groups to obtain a third total primary care visit number. By way of example, if the control circuit 210 determines in step 325 that the total number of people residing in a given geographic area is 100,000 and then determines in step 340 that the percentage of that are in poor health is 5%, that are in fair health is 25%, that are in good health is 40%, and that are in excellent health is 30%, and then determines in step 345 that the number of recommended primary care health care visits annually for people in the poor health group is 4, in the fair health group is 3, in the good health group is 2, and in the excellent health group is 1, then the third total primary care visit demand number calculated by the control circuit 210 (which indicates the primary care health care visit demand of people living in the selected geographic area) would be (100,000*0.05*4)+(100,000*0.25*3)+(100,000*0.40*2)+(100,000*0.30*1)=205,000 primary care visits within the selected period of time.

In the exemplary process 300 of FIG. 3A, after the control circuit 210 of the computing device 210 calculates the first, second and third total primary care visit demand numbers in steps 320, 335, and 345, respectively, the control circuit 210 is programmed to calculate an estimated unmet primary care visit demand in step 350 by determining the average of these three numbers (step 350). In the examples discussed above, after the control circuit 210 determines that the first total primary care annual visit demand number (calculated in box 320) is 90,000, the second total primary care annual visit demand number (calculated in box 335) is 30,000, and that the third total primary care annual visit demand number (calculated in box 345) is 205,000, then the net primary visit annual demand for the potential patients residing in the selected residential area is (90,000+30,000+205,000)/3=108,333 primary care visits per year.

In some embodiments, the control circuit 210 of the computing device 140 is programmed to estimate not just the primary care visit demand, but also the constrained primary care service provider supply. To that end, in step 355, the control circuit 210 of the computing device 140 is programmed to obtain electronic data representing the total number of the active primary care service providers (e.g., physicians) located in the selected geographic area. This data may be obtained by the control circuit 210, for example, from the exemplary health care service provider database 160 depicted in FIG. 1, which, as mentioned above, may be electronic data (which may be provided by/obtained from, for example, from sources such as the national provider index (NPI), etc.) indicative of names and addresses of every medical service provider offering primary care services in a given geographic area.

After obtaining the electronic data representing the total number of the active primary care service providers (e.g., physicians) located in the selected geographic area in step 355, the control circuit 210 is programmed to estimate in step 360 the total number of primary care health care visits that can be accommodated by the active primary care service providers (i.e., total visit capacity of the primary care service providers) located in the selected geographic area. The estimation performed by the control circuit 210 in step 360 may be based at least in part on the data obtained by the control circuit 210 from the health care service provider database 160 (which may include health care/medical sources including but not limited to Annals of Family Medicine, etc.). In one aspect, the control circuit 210 may be programmed to factor in the volume sizing assumption and calculate an estimated total primary care visit capacity of the active primary care service providers in the selected geographic area with a selected window of time by multiplying a total number of doctors associated with each of the health care service providers in the selected geographic area by a number of hours in a work day and by a total number of the potential patients that the doctors associated with each of the primary care service providers in the selected geographic area are predicted by the control circuit 210 to accommodate per hour.

In one example, when the control circuit 210 determines that the selected geographic area has 200 active work days for each primary care physician, the control circuit 210 is programmed to utilize an assumption that the physician works 8 hours per day and sees 3 existing patients per hour (20 minutes per appointment) 85% of the time and 1.33 new patients per hour (45 minutes per appointment) 15% of the time. As such, using this total primary care visit capacity model, the control circuit 210 would calculate in step 360 that the total visit capacity of each active primary care service provider in the selected geographic area is 200*[(8*0.85*3)+(8*0.15*1.33)]=4,400 annual primary care health care visits. If there are, for example, 30 primary care service providers in the selected geographic area, then the total visit capacity of these primary care service providers annually would be 4,400*30=132,000. It will be appreciated that the control circuit 210 may be programmed to perform the estimated total primary care visit capacity calculation/estimation based on a different algorithm (e.g., one determined over time by machine learning (e.g., convolutional neural networks or the like) to be more precise at estimating the total primary care visit capacity of the active primary care service providers within a selected geographic area in a given window of time).

In some aspects, after making the volume sizing assumption (i.e., estimating the total visit capacity of the primary care service providers), the control circuit 210 is programmed to factor in the primary care service provider supply constraint. In the exemplary process 300 depicted in FIG. 3A, the control circuit 210 is programmed to factor in the primary care service provider supply constraint, and calculate, based on the electronic data obtained from the electronic database 120, a primary care service provider constraint ratio (see step 365). In one approach, the primary care service provider constraint ratio is calculated by the control circuit as follows.

First, the control circuit 210 estimates a total number of visits, within the selected window of time, to active primary care service providers located in the selected geographic area by potential patients that reside in the selected geographic area. This estimation by the control circuit 210 may be performed based on data obtained from various medical claims data/analytics sources (e.g., PerceptionHealth® or the like) coupled to the electronic database 120. Second, the control circuit 210 estimates a total number of visits, within the selected window of time, to the active primary care service providers located in the selected geographic area by both the potential patients that reside in the selected geographic area and the potential patients that reside in at least one geographic area adjacent the selected geographic area. This estimation by the control circuit 210 may be performed based on data obtained from various medical claims data/analytics sources (e.g., PerceptionHealth® or the like) coupled to the electronic database 120. Third, the control circuit 210 calculates the primary care service provider constraint ratio in step 365 by dividing the total number of visits, within the selected window of time, to the active primary care service providers located in the selected geographic area by potential patients that reside in the selected geographic area by the total number of visits, within the selected window of time, to the active primary care service providers located in the selected geographic area by both the potential patients that reside in the selected geographic area and those that reside in the at least one geographic area adjacent the selected geographic area. In one example, if the 30 primary care service providers in the selected geographic area are estimated to be seeing 75000 patients that reside in the selected geographic area and 25000 patients that reside outside of the selected geographic area, then the control circuit 210 would calculate the primary care service provider supply constraint ratio to be 75000/(75,000+25,000)=0.75.

In some embodiments, the control circuit 210 may be programmed to obtain electronic data indicative which medical care service provider each of the potential patients in the region 400 has seen within a selected window of time (e.g., 3 months, 6 months, 1 year, 2 years, etc.), and, based on this data, estimate where (i.e., which geographic area 401-410) each of the potential patient resides. In some aspects, the control circuit 210 may be programmed to obtain electronic data representative of all of the health care visits associated with a given person, analyzes this data to determine how many times this patient has seen each of the health care providers in the region, and, based on this analysis, generates a ranking of the health care service providers (with the health care service providers that the patient has seen most being at the top). In one implementation, the control circuit 210 is programmed to select a predetermined number of the top health care providers (e.g., 5 providers) in the generated rankings, and then estimates that the patient resides (or works) at a location that is at the center of a plot containing these top ranked health care providers.

In the embodiment shown in FIG. 3A, in step 370, the control circuit 210 is further programmed to factor in the constrained primary care service provider (physician) supply by multiplying the total number of the active primary care service providers located in the selected geographic area (obtained in step 355) by the total number of primary care health care visits that can be accommodated by the active primary care service providers located in the selected geographic area (obtained/estimated in step 360) and by the primary care service provider constraint ratio (obtained/calculated in step 365). In the examples discussed above, after the control circuit 210 determines that the total number of active primary care service providers located in the selected geographic area is 30, and that the total number of primary care health care visits that can be accommodated by the active primary care service providers located in the selected geographic area is 4,400, and that the primary care service provider constraint ratio is 0.75, then the control circuit 210 would estimate in step 370 that the constrained primary care service provider visit supply (annually) for the potential patients residing in the selected residential area is 30*4,400*0.75=99,000 available primary care visits for the potential patients residing in this geographic area.

After the unmet primary care visit demand is estimated by the control circuit 210 at step 350, and after the constrained primary care service provider supply is estimated by the control circuit 210 at step 370, the process 300 depicted in FIG. 3A includes the step of estimating the net primary care visit demand by the potential patients residing in the geographic area of interest. In particular, in step 375, the control circuit 210 is programmed to subtract the constrained primary care service provider supply estimated in step 370 from the unmet primary care visit demand estimated at step 350 to arrive at the estimated net primary care visit demand. In the examples discussed above, where the unmet primary care visit demand was estimated to be 108,133 and the constrained primary care service provider supply was estimated by the control circuit 210 to be 99,000, the estimated net primary care visit demand is 9,133 visits per year. As mentioned above, the control circuit 210 may be programmed, in response to the calculation of the estimated net primary care visit demand for each geographic area of interest in step 375, to generate, on the display screen 260 of the computing device 140, a graphical interface including a visual representation of the result for each of the geographic area analyzed.

FIG. 5A represents an exemplary screenshot of a graphical table generated within a graphical interface 500 in connection with the region 400 depicted in FIG. 4A. The exemplary graphical interface 500 illustrates the net primary care demand (listed in field 503) for stores 1-10 (listed in field 501) located in geographic areas of interest 401-410

(listed in field 502). In some embodiments, the control circuit 210 is programmed with certain preset thresholds to generate an indicator (e.g., high demand (H), medium demand (M), low demand (L)) of net primary care visit demand in graphical field 503. In one aspect, the control circuit 210 is programmed to generate a low demand indicator (L) if the net primary care visit demand is below 0, generate a medium demand indicator (M) if the net primary care visit demand is between 5,000 and 25,000, and generate a high demand indicator (H) if the net primary care visit demand is above 25,000. It will be appreciated that the association of the net primary care visit demand numbers with high, medium, and low demand indicators by the control circuit 210 may be adjusted as necessary for a given geographic area of interest. As can be seen in FIG. 5A, the results generated in the graphical interface 500 of FIG. 5A show that geographic areas 401, 402, 404, and 407 have a low net primary care visit demand, geographic areas 405, 406, and 408 have a medium net primary care visit demand, and geographic areas 403, 409, and 410 have a high net primary care visit demand. In some embodiments, the graphical interface 500 may be transmitted via an electronic signal by the computing device 140 over the network 130 to the user computing device 145 to provide informational notifications/alerts to the user (e.g., a national manager, regional manager, or supercenter manager, etc.) of the user computing device 145 with respect to the estimated net health care demand in one or more geographic areas.

With reference to FIG. 3A, in some embodiments, the control circuit 210 is programmed to take a responsive action in response to the calculation of the estimated net primary care visit demand in order to ensure that the retailer optimizes the number of primary care service providers offered by the retailer in the geographic area of interest (step 379). For example, in some embodiments, the control circuit 210 may be programmed, in step 379, to generate an output, which may be generated on the visual display 260 or via the speaker 280 of the user interface 250 of the computing device 140, and which would inform the user of the computing device 140 whether the net primary care visit demand estimation by the control circuit 210 indicates that the health care visit capacity of health care service providers in the selected geographic area should be increased or reduced to optimize the health care service provider operations offered by the retailer. In some embodiments, the increases in health care capacity of the retailer in a given geographic area recommended by the control circuit 210 in step 379 may be dependent on the retailer-desired/set health care volume thresholds and on clinical capacity of the retailer (which may be pre-programmed into the control circuit 210).

FIG. 5B represents an exemplary screenshot of a graphical menu output (e.g., a recommendation) 512 that may be generated by the control circuit 210 in step 379 within an exemplary graphical interface 510. This recommendation output 512 shown in FIG. 5B may be generated in connection with any geographic area (i.e., any of geographic areas 401-410 of FIG. 4A) analyzed by the control circuit 210 for estimated net demand for health care visits (which, as mentioned above, may include primary care visits, dental visits, optometry visits, emergency visits, etc.). The exemplary graphical interface 510 in FIG. 5B includes a field 514 that indicates that recommendation of whether to increase health care operations in the analyzed geographic area. In the example shown in FIG. 5B, the recommendation in field 514 is indicated as "Build," followed by the estimated certainty of the control circuit 210 in this recommendation, which in FIG. 5B happens to be 90%.

The exemplary graphical interface 510 in FIG. 5B further includes a field 516 that indicates the health care model associated with the recommendation by the control circuit 210 to increase operations of the retailer in. In the example shown in FIG. 5B, the field 516 indicates that the control circuit 210 has generated a recommendation that the retailer increase operations in primary care services, dental care services, vision services, and emergency services. In the example shown in FIG. 5B, each of the health care models recommended by the control circuit 210 to increase health care operations in is followed by a percentage that reflects the recommendation certainty estimated by the control circuit 210 (which happens to be 95% in the case of primary care services, 60% in the case of dental care services, 80% in the case of vision care services, and 95% in the case of emergency care services).

The exemplary graphical interface 510 in FIG. 5B further includes a field 518 that indicates the financial health estimated by the control circuit 210 in association with the recommended health care models listed in field 516. In the exemplary graphical interface 510 shown in FIG. 5B, the financial health projection in field 516 is "Excellent," but, depending on various thresholds programmed into the control circuit 210, the financial health projection in field 516 may be Good, Fair, Poor, etc. In some embodiments, the graphical interface 510 may be transmitted via an electronic signal by the computing device 140 over the network 130 to the user computing device 145 to provide informational notifications/alerts to the user (e.g., a national manager, regional manager, or supercenter manager, etc.) of the user computing device 145 with respect to the recommendations of the control circuit 210 of the computing device 140 as to whether to increase or decrease health care operations of the retailer in one or more geographic areas.

It should be appreciated that the fields 514, 516, and 518 are shown in FIG. 5B by way of example only, and that some of these fields may be omitted from the graphical interface 510 in some implementations, and that additional fields may be added to the graphical interface 510 in other implementations. For example, in some embodiments, the exemplary graphical interface 510 may include a field reflecting the return on investment (ROI) estimated (e.g., by way of a percentage) by the control circuit 210 in association with the recommended health care models listed in field 516. In some embodiments, the exemplary graphical interface 510 may include a field reflecting the break-even point estimated (e.g., in terms of years) by the control circuit 210 in association with the recommended health care models listed in field 516.

This responsive action and output of the control circuit 210 may advantageously result in an increased primary care service provider presence in certain underserved communities that are in high need of primary care services, and may also advantageously result in operations cost savings for the retailer by reducing primary care services in certain communities, where the retailer has too many primary care service providers that are underutilized, and which would be advantageously deployed in other geographic areas.

The process 300 described in FIG. 3A may be performed by factoring in the question of whether the potential patients have insurance coverage or not (i.e., such that the only potential patients that are analyzed are those that are known to have insurance coverage), or may be performed without giving any weight to the question of whether the potential patients have insurance coverage or not (e.g., to serve underprivileged communities that are not adequately supported by primary care service providers and/or to attract additional cash-paying customers).

Figure 3B:
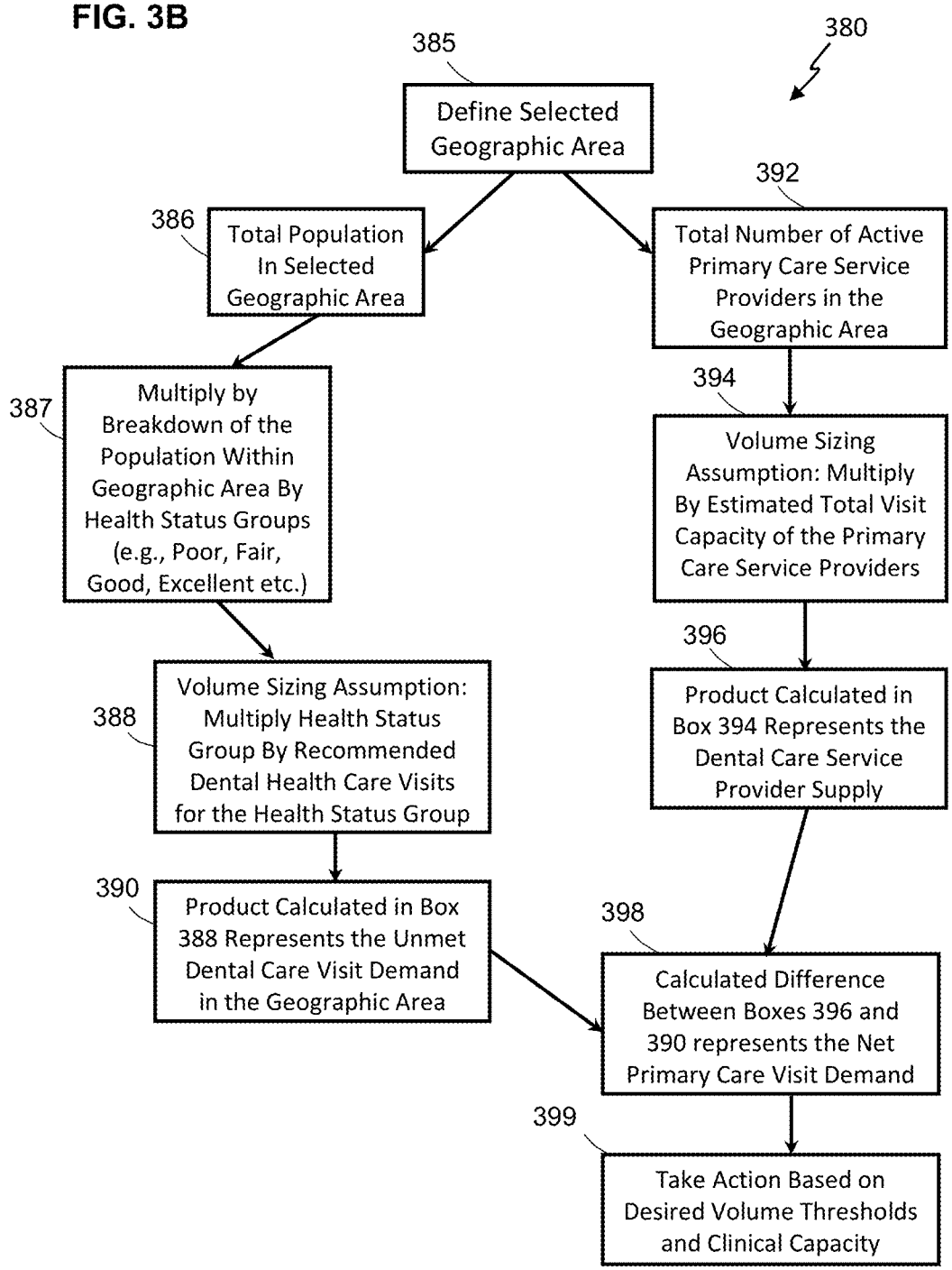
FIG. 3B is a diagram representing an overview flow chart of an exemplary process of estimating a net dental care visit demand of potential patients located in one or more geographic areas in accordance with some embodiments.

Notably, while FIG. 3A shows an exemplary process 300 of estimating a net primary care visit demand (i.e., a net demand of potential patients in a given geographic area for appointments with medical doctors), the control circuit 210 may be programmed in some embodiments to estimate a net dental care visit demand of the potential patients living in the same geographic area. In one exemplary process flow 380 illustrated in FIG. 3B, the control circuit 210 of the computing device 140 defines/draws a selected geographic area where the net dental care visit demand of the residents will be analyzed (step 385). Step 385 in FIG. 3B is substantially similar in terms of analysis and evaluation by the control circuit 210 in step 310 in FIG. 3A.

After defining/drawing the selected geographic area of interest in step 385 of FIG. 3B, the control circuit 210 may be programmed to obtain, in step 387, electronic data from the electronic database 120 representing the total number of people (i.e., potential patients) that reside in the selected geographic area, as well as electronic data indicating a breakdown of the potential patients located in the selected geographic area by a plurality of overall dental health status groups (e.g. Poor, Fair, Good, Excellent, etc.). This electronic data may be obtained by the control circuit 210 from the potential patient database 150 (which, as mentioned above, may include various health care data/analytics resources). In one aspect, the control circuit 210 is programmed to multiply the total number of the potential patients in each of the dental health status groups by the percentage of the potential patients located in the selected geographic area and classified in each of the dental health status groups.

In certain implementations, the control circuit 210 is programmed to obtain (in step 388) electronic data from the electronic database 120 representing the total number of dental health care visits recommended within the selected window of time for the potential patients in each of the dental health status groups. This data may be obtained by the control circuit 210, e.g., from the health visit recommendation database 170 (which may include data from sources including but not limited to American Dental Association, National Institute of Health, etc.). After obtaining this data, the control circuit 210 is also programmed to factor in the volume sizing assumption in step 388 by multiplying the total number of the potential patients in each of the dental health status groups by (1) the percentage of the potential patients located in the selected geographic area and classified in each of the dental health status groups; and (2) by the total number of dental health care visits recommended within the selected window of time for the potential patients classified in each of the dental health status groups. The product of this multiplication processed by the control circuit 210 represents the value of the estimated unmet dental care visit demand in the selected geographic area (step 390).

By way of example, if the control circuit 210 determines that the total number of people residing in a given geographic area is 50,000 and then determines that the percentage of that are in poor dental health is 5%, that are in fair dental health is 25%, that are in good dental health is 40%, and that are in excellent dental health is 30%, and then determines that the number of recommended dental health care visits annually for people in the poor dental health group is 4, in the fair dental health group is 3, in the good dental health group is 2, and in the excellent dental health group is 1, then the unmet dental health care visit demand of people living in the selected geographic area would be (50,000*0.05*4)+(50,000*0.25*3)+(50,000*0.40*2)+(50,000*0.30*1)=102,500 dental health care visits within the selected period of time.

In some embodiments, the control circuit 210 of the computing device 140 is programmed to estimate not just the dental care visit demand in one or more geographic areas, but also the dental service provider supply. To that end, the control circuit 210 of the computing device 140 may be programmed to obtain (step 392) electronic data representing the total number of active dental service providers (e.g., dentists) located in the selected geographic area. This data may be obtained by the control circuit 210, for example, from the exemplary health care service provider database 160 depicted in FIG. 1, which, as mentioned above, may be electronic data (e.g., a state or national registry) indicative of names and addresses and status (active/not active) of the dentists offering dental care services in a given geographic area.

In some implementations, after obtaining the electronic data representing the total number of the active dental care service providers located in the selected geographic area in step 392, the control circuit 210 is programmed to estimate (in step 394) the total number of dental care visits that can be accommodated by the active dental care service providers (i.e., total visit capacity of the dental care service providers) located in the selected geographic area. The estimation performed by the control circuit 210 in step 394 may be based at least in part on the data obtained by the control circuit 210 from the health care service provider database 160 (which may be obtained from data compilation/analytics sources including but not limited to Agency for Health Care Research and Quality (AHRQ)). In one aspect, the control circuit 210 may be programmed to factor in, in step 394, the volume sizing assumption and estimate/calculate the total visit capacity of the active dental care service providers in the selected geographic area with a selected window of time by multiplying a total number of active dentists in the selected geographic area by a number of hours in a typical workday and by a total number of the potential patients that the dentists in the selected geographic area are predicted by the control circuit 210 to accommodate per hour.

In one example, when the control circuit 210 determines that the selected geographic area has 200 active workdays for each dentist, the control circuit 210 is programmed to utilize an assumption that the dentist works 8 hours per day and sees 2 existing patients per hour (30 minutes per appointment) 90% of the time and 1 new dental patients per hour (1 hour per appointment) 10% of the time. As such, using this total dental visit capacity estimation model, the control circuit 210 would estimate/calculate that the total visit capacity of each active dental care service provider in the selected geographic area is 200*[(8*0.9*2)+(8*0.1*1)] =3,040 annual dental care health care visits. If there are, for example, 30 dental care service providers in the selected geographic area, then the total visit capacity of these dental care service providers annually would be 3,040*30=91,200. It will be appreciated that the control circuit 210 may be programmed to perform the estimated total dental visit capacity calculation in step 394 based on a different preprogrammed algorithm (e.g., one determined over time by machine learning (e.g., convolutional neural networks, etc.) to be more precise at estimating the total visit capacity of the active dental care service providers within a selected geographic area in a given window of time).

In some implementations, after making the volume sizing assumption (i.e., estimating the total visit capacity of the dental care service providers), the control circuit 210 may factor in the dental care service provider supply constraint akin to the primary care service provider supply constraint ratio described above in reference to step 365 in FIG. 3A. Factoring in the dental care service provider supply constrain may provide a better indication of the net dental care visit supply for the residents of the geographic area of interest by accounting for the fact that not all dental care visits services by the dental care health providers in a given geographic area are available to the residents of this geographic area, but that a certain percentage of these dental care health care visits are taken up by residents of one or more geographic areas adjacent the geographic area of interest (especially when it comes to dental care service providers located near the outskirts of the geographic area of interest and near the border with adjacent geographic areas.

In some embodiments, after the unmet dental care visit demand is estimated by the control circuit 210 in step 290 and after the dental care visit supply is estimated by the control circuit 210 in step 396, the control circuit 210 is programmed, in step 398, to subtract the dental care service provider supply from the unmet dental care visit demand to arrive at the estimated net dental care visit demand. In the above example, where the unmet dental care visit demand was determined to be 102,500 and the dental care service provider supply was estimated by the control circuit 210 to be 99,000, the estimated net dental care visit demand is 3,500 visits per year.

As mentioned above, the control circuit 210 may be programmed, in response to the calculation of the estimated net dental care visit demand for each geographic area of interest, to generate, on the display screen 260 of the computing device 140, a graphical interface including a visual representation of the result for each of the geographic area analyzed.

With reference to FIG. 3B, in some embodiments, the control circuit 210 is programmed to take a responsive action in response to the calculation of the estimated net dental care visit demand in order to ensure that the retailer optimizes the number of dental care service providers offered by the retailer in the geographic area of interest (step 399). For example, in some embodiments, the control circuit 210 may be programmed, in step 399, to generate an output, which may be generated on the visual display 260 or via the speaker 280 of the user interface 250 of the computing device 140, and which would inform the user of the computing device 140 whether the net dental care visit demand estimation by the control circuit 210 indicates that the dental care visit capacity of health care service providers in the selected geographic area should be increased or reduced to optimize the dental care service provider operations offered by the retailer. For example, depending on the thresholds programmed into the control circuit 210, upon estimating that the net dental care visit demand is 3,500 visits per year, the control circuit 210 may be programmed to generate, in step 399, an output indicating a need for increasing the dental care visit capacity of the dental service providers in the selected geographic area (i.e., if the threshold net dental care visit demand for triggering an increase in dental services is set below 3,500), or to generate an output indicating that there is no need for increasing the dental care visit capacity of the dental service providers in the selected geographic area (i.e., if the threshold dental care visit demand for triggering an increase in dental services is set above 3,500).

Given that medical and dental demand varies over time in many geographic regions/areas (due to people moving in and out), in some embodiments, the control circuit 210 may be programmed to run periodic estimations (e.g., quarterly, bi-annually, annually, etc.) of the net medical care visit demand/net dental care visit demand in the geographic areas of interest to ensure that the medical care/dental care services provided by the retailer are (1) sufficient to meet the current health care/dental care visit demand when the current medical care/dental care visit demand stays substantially the same relative to the last previously estimated medical care/dental care visit demand in this geographic area; (2) may be increased to meet the current health care/dental care visit demand when the current medical care/dental care visit demand has substantially increased relative to the last previously estimated medical care/dental care visit demand in this geographic area; and (3) may be reduced to cut unnecessary operation costs when the current medical care/dental care visit demand has substantially decreased relative to the last previously estimated medical care/dental care visit demand in this geographic area. As such, the control circuit 210 is programmed to maintain the medical care/dental care services provided by the retailer at an optimal level over an extended period of time.

With reference to FIG. 6, one method 600 of operation of the system 100 to estimate a net health care demand of potential patients located in one or more geographic areas is shown. For exemplary purposes, the method 600 is described in the context of the system of FIG. 1, but it is understood that embodiments of the method 600 may be implemented in this or other systems.

As shown in FIG. 6, the method 600 includes providing at least one electronic database 120 (which may include databases 150, 160, and 170 described above) configured to store electronic data that comprises at least one of: electronic information associated with the potential patients located in a selected geographic area; electronic information associated with health care service providers located in the selected geographic area; and electronic information associated with general health visit recommendations for the potential patients located in the selected geographic area (step 610).

The method 600 further includes providing a computing device 140 including a control circuit 210 having a programmable processor, which causes the computing device to obtain electronic data from the at least one electronic database 120 (step 620). In some aspects, as described above, the electronic data obtained by the control circuit 210 from the electronic database 120 may be obtained from one or more of the databases 150, 160, 170, and may include, but is not limited to: electronic information associated with the potential patients located in a selected geographic area; electronic information associated with health care service providers located in the selected geographic area; and electronic information associated with general health care visit recommendations for the potential patients located in the selected geographic area.

The method 600 further includes analyzing, by the control circuit 210, the electronic information associated with the potential patients located in a selected geographic area and the electronic information associated with general health visit recommendations in order to calculate an estimated total number of health care visits recommended for the potential patients located in the selected geographic area within a selected window of time (step 630). In addition, the method 600 includes analyzing, by the control circuit 210, the electronic information associated with the health care service providers located in the selected geographic area in order to calculate an estimated total number of health care visits that the health care service providers located in the selected geographic area can accommodate within the selected window of time (step 640).

Following steps 630 and 640, the exemplary method 600 of FIG. 6 further includes correlating, by the control circuit 210, the calculated estimated total number of the health care visits recommended for the potential patients located in the selected geographic area within the selected window of time with the calculated estimated total number of health care visits that the health care service providers located in the selected geographic area can accommodate within the selected window of time (step 650). After this correlation, and upon a determination by the control circuit that the calculated estimated total number of the health care visits recommended for the potential patients in the selected geographic area within the selected window of time is greater than the calculated estimated total number of the health care visits that the health care service providers in the selected geographic area can accommodate within the selected window of time, the method 600 includes generating an electronic output indicating a need for increasing the health care visit capacity of health care service providers in the selected geographic area (step 660). On the other hand, upon a determination by the control circuit that the calculated estimated total number of the health care visits recommended for the potential patients in the selected geographic area within the selected window of time is less than the calculated estimated total number of the health care visits that the health care service providers in the selected geographic area can accommodate within the selected window of time, the method 600 includes generating an electronic output indicating a need for reduction of the health care visit capacity of health care service providers in the selected geographic area (step 670).

The systems and methods described herein provide for various approaches/algorithms to accurately estimate and monitor the net health care demand of the population in a given geographic area. The reliability of the estimation of the net health care demand may be enhanced by the use of various electronic databases and data analytic modules, including, but not limited to predictive models, machine learning, and/or neural networks. As a result, the systems and methods described herein facilitate an optimal health care provider presence (and staffing) by the retailer in the geographic areas where the retailer is operational, but make the retailer aware of opportunities to expand health care coverage into new (e.g., currently underserved) geographic areas to increase profits, and make the retailer aware of geographic areas, where the health care provider operations (e.g., staffing, business hours, etc.) should be reduced in view of the low health care demand by the population in those geographic areas. As such, the systems and methods described herein are likely to substantially increase the efficiency and profit margins of the health care service operations of the retailer.

Those skilled in the art will recognize that a wide variety of other modifications, alterations, and combinations can also be made with respect to the above-described embodiments without departing from the scope of the invention, and that such modifications, alterations, and combinations are to be viewed as being within the ambit of the inventive concept.

What is claimed is:

1. A system for estimating a net health care demand of potential patients located in one or more geographic areas, the system comprising:

at least one electronic database configured to store electronic data that comprises at least one of:
  electronic information associated with the potential patients located in a selected geographic area, wherein the electronic information associated with the potential patients includes a profile of each of the potential patients, the profile of each of the potential patients comprising at least one of physical addresses of the potential patients, ages of the potential patients, health-related conditions of the potential patients, and general health status of the potential patients;
  electronic information associated with health care service providers located in the selected geographic area, wherein the electronic information associated with the health care service providers comprises at least one of physical addresses of the health care service providers and a total number of doctors associated with each of the health care service providers; and
  electronic information associated with general health care visit recommendations for the potential patients located in the selected geographic area, wherein the electronic information associated with the general health visit recommendations for the potential patients located in the selected geographic area includes health visit recommendations published by private health organizations, or city, county, state, and federal government health organizations;
a computing device including a control circuit having a programmable processor, the control circuit configured to:
  process an electronic map of a geographic region to define the selected geographic area by detecting a physical address of a selected health care provider within the selected geographic area and generating on the electronic map of the geographic region a visible boundary that surrounds the selected geographic area in which the physical address of the selected health provider is detected by the control circuit, wherein each point on the boundary is determined by the control circuit to be within a predetermined threshold driving time in minutes or a predetermining threshold driving distance in miles from the physical address of the selected health care provider detected by the control circuit;
  cause the computing device to obtain the electronic data from the at least one electronic database,
  load at least one of an algorithm and a business rule pre-programmed into the control circuit to process the electronic information associated with the potential patients located in the selected geographic area and the electronic information associated with general health care visit recommendations and calculate an estimated total number of health care visits recommended for the potential patients located in the selected geographic area within a selected window of time;
  load at least one of the algorithm and the business rule pre-programmed into the control circuit to process the electronic information associated with the health care service providers located in the selected geographic area and calculate an estimated total number of health care visits that the health care service providers located in the selected geographic area can accommodate within the selected window of time, wherein the control circuit is further configured to estimate the total number of the health care visits that the health care service providers in the selected geographic area can accommodate within the selected window of time by multiplying a total number of doctors associated with each of the health care service providers in the selected geographic area by a number of hours in a work day and by a total number of the potential patients that the doctors associated with each of the health care service providers in the selected geographic area are predicted by the control circuit to accommodate per hour;

correlate electronic data representing the calculated estimated total number of the health care visits recommended for the potential patients located in the selected geographic area within the selected window of time with electronic data representing the calculated estimated total number of health care visits that the health care service providers located in the selected geographic area can accommodate within the selected window of time;

upon a determination by the control circuit that the calculated estimated total number of the health care visits recommended for the potential patients in the selected geographic area within the selected window of time is greater than the calculated estimated total number of the health care visits that the health care service providers in the selected geographic area can accommodate within the selected window of time, generate an electronic output in a form of a graphical interface on a display screen of the computing device, the graphical interface including electronic data indicating a need for increasing the health care visit capacity of health care service providers in the selected geographic area; and upon a determination by the control circuit that the calculated estimated total number of the health care visits recommended for the potential patients in the selected geographic area within the selected window of time is less than the calculated estimated total number of the health care visits that the health care service providers in the selected geographic area can accommodate within the selected window of time, generate the electronic output in the form of the graphical interface on the display screen of the computing device, the graphical interface including electronic data indicating a need for reduction of the health care visit capacity of health care service providers in the selected geographic area;

wherein the electronic output generated by the control circuit includes table format data such that the graphical interface, when generated on the display screen of the computing device, includes a graphical table including the electronic data indicating a need for increasing or decreasing the health care visit capacity of health care service providers in the selected geographic area; and wherein the graphical interface is interactive in that the graphical user interface, when generated on the display screen of the computing device, includes:
  at least one electronic notification that provides a user of the computing device with information that a task has been assigned to the user; and
  at least one interactive field that requires the user of the computing device to enter a response to the at least one electronic notification and indicate that the at least one task assigned to the user has been performed.

2. The system of claim 1,
wherein the at least one electronic database is configured to store electronic information associated with potential patients located in at least one geographic area adjacent the selected geographic area; and
wherein the processor is programmed to:
  analyze a physical address of each of the potential patients stored in the at least one electronic database in order to determine a number of the potential patients located in a first geographic area and a number of the potential patients located in the at least a second geographic area adjacent the first geographic area;
  analyze a physical address of each of the health care service providers stored in the at least one electronic database in order to determine an identity of each of the health care service providers in the first geographic area and in the second geographic area; and
  estimate, based on the electronic data obtained from the at least one electronic database, a total number of visits, within the selected window of time, to a health care service provider located in the first geographic area by potential patients that reside in the first geographic area and by potential patients that reside in the second geographic area.

3. The system of claim 1, wherein the selected geographic area is defined as a perimeter that is estimated by the processor of the control circuit to be within a predetermined number of minutes of driving from a center of the selected geographic area.

4. A system for estimating a net health care demand of potential patients located in one or more geographic areas, the system comprising:
  at least one electronic database configured to store electronic data that comprises at least one of:
    electronic information associated with the potential patients located in a selected geographic area;
    electronic information associated with health care service providers located in the selected geographic area; and
    electronic information associated with general health care visit recommendations for the potential patients located in the selected geographic area;
  a computing device including a control circuit having a programmable processor, the control circuit configured to:
    process an electronic map of a geographic region to define the selected geographic area by detecting a physical address of a selected health care provider within the selected geographic area and generating on the electronic map of the geographic region a visible boundary that surrounds the selected geographic area in which the physical address of the selected health provider is detected by the control circuit, wherein each point on the boundary is determined by the control circuit to be within a predetermined threshold driving time in minutes or a predetermining threshold driving distance in miles from the physical address of the selected health care provider detected by the control circuit;
    cause the computing device to obtain the electronic data from the at least one electronic database,
    load at least one of an algorithm and a business rule pre-programmed into the control circuit to process the electronic information associated with the potential patients located in the selected geographic area and the electronic information associated with general health care visit recommendations and calculate an estimated total number of health care visits recommended for the potential patients located in the selected geographic area within a selected window of time;

load at least one of the algorithm and the business rule pre-programmed into the control circuit to process the electronic information associated with the health care service providers located in the selected geographic area and calculate an estimated total number of health care visits that the health care service providers located in the selected geographic area can accommodate within the selected window of time;

correlate electronic data representing the calculated estimated total number of the health care visits recommended for the potential patients located in the selected geographic area within the selected window of time with electronic data representing the calculated estimated total number of health care visits that the health care service providers located in the selected geographic area can accommodate within the selected window of time;

upon a determination by the control circuit that the calculated estimated total number of the health care visits recommended for the potential patients in the selected geographic area within the selected window of time is greater than the calculated estimated total number of the health care visits that the health care service providers in the selected geographic area can accommodate within the selected window of time, generate an electronic output in a form of a graphical interface on a display screen of the computing device, the graphical interface including electronic data indicating a need for increasing the health care visit capacity of health care service providers in the selected geographic area;

upon a determination by the control circuit that the calculated estimated total number of the health care visits recommended for the potential patients in the selected geographic area within the selected window of time is less than the calculated estimated total number of the health care visits that the health care service providers in the selected geographic area can accommodate within the selected window of time, generate the electronic output in the form of the graphical interface on the display screen of the computing device, the graphical interface including electronic data, indicating a need for reduction of the health care visit capacity of health care service providers in the selected geographic area;

wherein the electronic output includes table format data such that the graphical interface, when generated on the display screen of the computing device, includes a graphical table including the electronic data indicating a need for increasing or decreasing the health care visit capacity of health care service providers in the selected geographic area; and wherein the graphical interface is interactive in that the graphical user interface, when generated on the display screen of the computing device, includes:
at least one electronic notification that provides a user of the computing device with information that a task has been assigned to the user; and
at least one interactive field that requires the user of the computing device to enter a response to the at least one electronic notification and indicate that the at least one task assigned to the user has been performed;

obtain, from the at least one electronic database, the electronic information indicating:
a breakdown of the potential patients in the selected geographic area by a plurality of age groups and a number of recommended health care visits within the selected window of time for each of the age groups;
a total number of potential patients located in the selected geographic area;
a percentage of the potential patients located in the selected geographic area having a predetermined medical condition and a number of recommended health care visits within the selected window of time for the potential patients having the predetermined medical condition;
a breakdown of the potential patients located in the selected geographic area by a plurality of overall health status groups and a number of recommended health care visits within the selected window of time for each of the health status groups; and
a total number of active primary care service providers located in the selected geographic area; and
analyze the electronic information obtained from the at least one electronic database to determine an estimated unmet primary care visit demand of the potential patients located in the selected geographic area within the selected window of time.

5. The system of claim 4, wherein the processor of the control circuit is further configured to:
obtain, from the at least one electronic database, a total number of the health care visits recommended within the selected window of time for each of the age groups located within the selected geographic area, and multiply a total number of the potential patients in each of the age groups by the number of the health care visits recommended within the selected window of time for each one of the age groups to obtain a first total primary care visit demand number;
obtain, from the at least one electronic database, a total number of health care visits recommended within the selected window of time for the potential patients having the predetermined medical condition and located within the selected geographic area, and multiply a total number of the potential patients located in the geographic area by the percentage of the potential patients located in the selected geographic area having the predetermined medical condition and further multiply by the total number of health care visits recommended within the selected window of time for the potential patients having the predetermined medical condition to obtain a second total primary care visit demand number;
obtain, from the at least one electronic database, a total number of health care visits recommended within the selected window of time for each of the health status groups located within the selected geographic area, and multiply a total number of the potential patients in each of the health status groups by the percentage of the potential patients located in the selected geographic area and classified in each of the health status groups, and further multiply by the total number of health care visits recommended within the selected window of time for the potential patients classified in each of the health status groups to obtain a third total primary care visit demand number; and calculate the estimated unmet primary care visit demand by determining an average of the first, second, and third total primary care visit demand numbers.

6. The system of claim 5, wherein the processor of the control circuit is further configured to:

obtain, from the at least one electronic database, the total number of the active primary care service providers located in the selected geographic area;

obtain, from the at least one electronic database, a total number of health care visits that can be accommodated by the active primary care service providers located in the selected geographic area;

calculate, based on the electronic data obtained from the at least one electronic database, a primary care service provider constraint ratio by dividing:

a total number of visits, within the selected window of time, to active primary care service providers located in the selected geographic area by potential patients that reside in the selected geographic area; by a total number of visits, within the selected window of time, to the active primary care service provider located in the selected geographic area by both the potential patients that reside in the selected geographic area and the potential patients that reside in the at least one geographic area adjacent the selected geographic area;

calculate a constrained primary care service provider visit supply by multiplying the total number of the active primary care service providers located in the selected geographic area by the total number of health care visits that can be accommodated by the active primary care service providers located in the selected geographic area and by the primary care service provider constraint ratio.

7. The system of claim 6, wherein the processor of the control circuit is further configured to calculate an estimated net primary care visit demand of the potential patients in the selected geographic area by subtracting the constrained primary care provider visit supply calculated by the processor from the estimated unmet primary care visit demand determined by the processor.

8. The system of claim 1, wherein the health care visits include medical visits and dental visits.

9. A method of estimating a net health care demand of potential patients located in one or more geographic areas, the method comprising:

providing at least one electronic database configured to store electronic data that comprises at least one of:

electronic information associated with the potential patients located in a selected geographic area, wherein the electronic information associated with the potential patients includes a profile of each of the potential patients, the profile of each of the potential patients comprising at least one of physical addresses of the potential patients, ages of the potential patients, health-related conditions of the potential patients, and general health status of the potential patients;

electronic information associated with health care service providers located in the selected geographic area, wherein the electronic information associated with the health care service providers comprises at least one of physical addresses of the health care service providers and a total number of doctors associated with each of the health care service providers; and electronic information associated with general health visit recommendations for the potential patients located in the selected geographic area, wherein the electronic information associated with the general health visit recommendations for the potential patients located in the selected geographic area includes health visit recommendations published by private health organizations, or city, county, state, and federal government health organizations; providing a computing device including a control circuit having a programmable processor; by the control circuit:

processing an electronic map of a geographic region to define the selected geographic area by detecting a physical address of a selected health care provider within the selected geographic area and generating on the electronic map of the geographic region a visible boundary that surrounds the selected geographic area in which the physical address of the selected health provider is detected by the control circuit, wherein each point on the boundary is determined by the control circuit to be within a predetermined threshold driving time in minutes or a predetermining threshold driving distance in miles from the physical address of the selected health care provider detected by the control circuit;

causing the computing device to obtain the electronic data from the at least one electronic database, loading at least one of an algorithm and a business rule pre-programmed into the control circuit to process the electronic information associated with the potential patients located in the selected geographic area and the electronic information associated with general health visit recommendations and calculate an estimated total number of health care visits recommended for the potential patients located in the selected geographic area within a selected window of time;

loading at least one of the algorithm and the business rule pre-programmed into the control circuit to process the electronic information associated with the health care service providers located in the selected geographic area and calculate an estimated total number of health care visits that the health care service providers located in the selected geographic area can accommodate within the selected window of time, wherein the control circuit is further configured to estimate the total number of the health care visits that the health care service providers in the selected geographic area can accommodate within the selected window of time by multiplying a total number of doctors associated with each of the health care service providers in the selected geographic area by a number of hours in a work day and by a total number of the potential patients that the doctors associated with each of the health care service providers in the selected geographic area are predicted by the control circuit to accommodate per hour;

correlating electronic data representing the calculated estimated total number of the health care visits recommended for the potential patients located in the selected geographic area within the selected window of time with electronic data representing the calculated estimated total number of health care visits that the health care service providers located in the selected geographic area can accommodate within the selected window of time;
upon a determination by the control circuit that the calculated estimated total number of the health care visits recommended for the potential patients in the selected geographic area within the selected window of time is greater than the calculated estimated total number of the health care visits that the health care service providers in the selected geographic area can accommodate within the selected window of time, generating an electronic output in a form of a graphical interface on a display screen of the computing device, the graphical interface including electronic data indicating a need for increasing the health care visit capacity of health care service providers in the selected geographic area; and
upon a determination by the control circuit that the calculated estimated total number of the health care visits recommended for the potential patients in the selected geographic area within the selected window of time is less than the calculated estimated total number of the health care visits that the health care service providers in the selected geographic area can accommodate within the selected window of time, generating the electronic output in a form of the graphical interface on the display screen of the computing device, the graphical interface including electronic data indicating a need for reduction of the health care visit capacity of health care service providers in the selected geographic area;
wherein the electronic output includes table format data such that the graphical interface, when generated on the display screen of the computing device, includes a graphical table including the electronic data indicating a need for increasing or decreasing the health care visit capacity of health care service providers in the selected geographic area; and
wherein the graphical interface is interactive in that the graphical user interface, when generated on the display screen of the computing device, includes:
at least one electronic notification that provides a user of the computing device with information that a task has been assigned to the user; and
at least one interactive field that requires the user of the computing device to enter a response to the at least one electronic notification and indicate that the at least one task assigned to the user has been performed.

10. The method of claim 9,
wherein the at least one electronic database is configured to store electronic information associated with potential patients located in at least one geographic area adjacent the selected geographic area; and
further comprising, by the control circuit:
analyzing a physical address of each of the potential patients stored in the at least one electronic database in order to determine a number of the potential patients located in a first geographic area and a number of the potential patients located in the at least a second geographic area adjacent the first geographic area;
analyzing a physical address of each of the health care service providers stored in the at least one electronic database in order to determine an identity of each of the health care service providers in the first geographic area and in the second geographic area; and
estimating, based on the electronic data obtained from the at least one electronic database, a total number of visits, within the selected window of time, to a health care service provider located in the first geographic area by potential patients that reside in the first geographic area and by potential patients that reside in the second geographic area.

11. The method of claim 9, wherein the selected geographic area is defined as a perimeter that is estimated by the processor of the control circuit to be within a predetermined number of minutes of driving from a center of the selected geographic area.

12. A method of estimating a net health care demand of potential patients located in one or more geographic areas, the method comprising:
providing at least one electronic database configured to store electronic data that comprises at least one of:
electronic information associated with the potential patients located in a selected geographic area;
electronic information associated with health care service providers located in the selected geographic area; and
electronic information associated with general health visit recommendations for the potential patients located in the selected geographic area;
providing a computing device including a control circuit having a programmable processor; by the control circuit:
processing an electronic map of a geographic region to define the selected geographic area by detecting a physical address of a selected health care provider within the selected geographic area and generating on the electronic map of the geographic region a visible boundary that surrounds the selected geographic area in which the physical address of the selected health provider is detected by the control circuit, wherein each point on the boundary is determined by the control circuit to be within a predetermined threshold driving time in minutes or a predetermining threshold driving distance in miles from the physical address of the selected health care provider detected by the control circuit;
causing the computing device to obtain the electronic data from the at least one electronic database,
loading at least one of an algorithm and a business rule pre-programmed into the control circuit to process the electronic information associated with the potential patients located in the selected geographic area and the electronic information associated with general health visit recommendations and calculate an estimated total number of health care visits recommended for the potential patients located in the selected geographic area within a selected window of time;
loading at least one of an algorithm and a business rule pre-programmed into the control circuit to process the electronic information associated with the health care service providers located in the selected geographic area and calculate an estimated total number of health care visits that the health care service providers located in the selected geographic area can accommodate within the selected window of time;
correlating the electronic data representing calculated estimated total number of the health care visits recommended for the potential patients located in the selected geographic area within the selected window of time with electronic data representing the calculated estimated total number of health care visits that the health care service providers located in the selected geographic area can accommodate within the selected window of time;

upon a determination by the control circuit that the calculated estimated total number of the health care visits recommended for the potential patients in the selected geographic area within the selected window of time is greater than the calculated estimated total number of the health care visits that the health care service providers in the selected geographic area can accommodate within the selected window of time, generating an electronic output in a form of a graphical interface on a display screen of the computing device, the graphical interface including electronic data indicating a need for increasing the health care visit capacity of health care service providers in the selected geographic area; and upon a determination by the control circuit that the calculated estimated total number of the health care visits recommended for the potential patients in the selected geographic area within the selected window of time is less than the calculated estimated total number of the health care visits that the health care service providers in the selected geographic area can accommodate within the selected window of time, generating the electronic output in the form of the graphical interface on the display screen of the computing device, the graphical interface including electronic data indicating a need for reduction of the health care visit capacity of health care service providers in the selected geographic area;

wherein the electronic output includes table format data such that the graphical interface, when generated on the display screen of the computing device, includes a graphical table including the electronic data indicating a need for increasing or decreasing the health care visit capacity of health care service providers in the selected geographic area; and wherein the graphical interface is interactive in that the graphical user interface, when generated on the display screen of the computing device, includes:
  at least one electronic notification that provides a user of the computing device with information that a task has been assigned to the user; and
  at least one interactive field that requires the user of the computing device to enter a response to the at least one electronic notification and indicate that the at least one task assigned to the user has been performed;

obtaining, from the at least one electronic database, the electronic information indicating:
  a breakdown of the potential patients in the selected geographic area by a plurality of age groups and a number of recommended health care visits within the selected window of time for each of the age groups;
  a total number of potential patients located in the selected geographic area;
  a percentage of the potential patients located in the selected geographic area having a predetermined medical condition and a number of recommended health care visits within the selected window of time for the potential patients having the predetermined medical condition;
  a breakdown of the potential patients located in the selected geographic area by a plurality of overall health status groups and a number of recommended health care visits within the selected window of time for each of the health status groups; and
  a total number of active primary care service providers located in the selected geographic area; and
analyzing the electronic information obtained from the at least one electronic database to determine an estimated unmet primary care visit demand of the potential patients located in the selected geographic area within the selected window of time.

13. The method of claim 12, further comprising, by the control circuit:
  obtaining, from the at least one electronic database, a total number of the health care visits recommended within the selected window of time for each of the age groups located within the selected geographic area, and multiplying a total number of the potential patients in each of the age groups by the number of the health care visits recommended within the selected window of time for each one of the age groups to obtain a first total primary care visit demand number;
  obtaining, from the at least one electronic database, a total number of health care visits recommended within the selected window of time for the potential patients having the predetermined medical condition and located within the selected geographic area, and multiplying a total number of the potential patients located in the geographic area by the percentage of the potential patients located in the selected geographic area having the predetermined medical condition and further multiplying by the total number of health care visits recommended within the selected window of time for the potential patients having the predetermined medical condition to obtain a second total primary care visit demand number;
  obtaining, from the at least one electronic database, a total number of health care visits recommended within the selected window of time for each of the health status groups located within the selected geographic area, and multiplying a total number of the potential patients in each of the health status groups by the percentage of the potential patients located in the selected geographic area and classified in each of the health status groups, and further multiplying by the total number of health care visits recommended within the selected window of time for the potential patients classified in each of the health status groups to obtain a third total primary care visit demand number; and
  calculating the estimated unmet primary care visit demand by determining an average of the first, second, and third total primary care visit demand numbers.

14. The method of claim 13, further comprising, by the control circuit:
  obtaining, from the at least one electronic database, the total number of the active primary care service providers located in the selected geographic area;
  obtaining, from the at least one electronic database, a total number of health care visits that can be accommodated by the active primary care service providers located in the selected geographic area;
  calculating, based on the electronic data obtained from the at least one electronic database, a primary care service provider constraint ratio by dividing:
    a total number of visits, within the selected window of time, to an active primary care service provider located in the selected geographic area by potential patients that reside in the selected geographic area; by a total number of visits, within the selected window of time, to the active primary care service provider located in the selected geographic area by both the potential patients that reside in the selected geographic area and the potential patients that reside in the at least one geographic area adjacent the selected geographic area;

calculating a constrained primary care service provider visit supply by multiplying the total number of the active primary care service providers located in the selected geographic area by the total number of health care visits that can be accommodated by the active primary care service providers located in the selected geographic area and by the primary care service provider constraint ratio.

15. The method of claim 14, further comprising, by the control circuit, calculating an estimated net primary care visit demand of the potential patients in the selected geographic area by subtracting the constrained primary care provider visit supply calculated by the processor from the estimated unmet primary care visit demand calculated by the processor.

16. The method of claim 9, wherein the health care visits include medical visits and dental visits.

* * * * *